(12) United States Patent
Andersen et al.

(10) Patent No.: US 7,842,294 B2
(45) Date of Patent: Nov. 30, 2010

(54) PROTEINS BELONGING TO THE BCL-2 FAMILY AND FRAGMENTS THEREOF, AND THEIR USE IN CANCER PATIENTS

(75) Inventors: Mads Hald Andersen, Hellerup (DK); Per Thor Straten, Hvidovre (DK)

(73) Assignee: Survac APS, Hellerup (DK)

( * ) Notice: Subject to any disclaimer, the term of this patent is extended or adjusted under 35 U.S.C. 154(b) by 946 days.

(21) Appl. No.: 10/580,016

(22) PCT Filed: Nov. 18, 2004

(86) PCT No.: PCT/DK2004/000799
§ 371 (c)(1),
(2), (4) Date: Feb. 28, 2007

(87) PCT Pub. No.: WO2005/049073
PCT Pub. Date: Jun. 2, 2005

(65) Prior Publication Data
US 2008/0050396 A1    Feb. 28, 2008

Related U.S. Application Data

(60) Provisional application No. 60/523,119, filed on Nov. 19, 2003.

(30) Foreign Application Priority Data
Nov. 19, 2003    (DK) ............................... 2003 01716

(51) Int. Cl.
*A61K 39/00*    (2006.01)
(52) U.S. Cl. .................................................. 424/184.1
(58) Field of Classification Search ........................ None
See application file for complete search history.

(56) References Cited

U.S. PATENT DOCUMENTS

| 5,470,955 A | 11/1995 | Craig |
| 5,789,201 A * | 8/1998 | Guastella .................... 435/69.1 |
| 5,856,171 A | 1/1999 | Korsmeyer |

FOREIGN PATENT DOCUMENTS

| WO | WO98/58541 | 12/1998 |
| WO | WO01/36594 A1 | 5/2001 |
| WO | WO 01/44282 A2 | 6/2001 |
| WO | WO 02/05835 | 1/2002 |
| WO | WO 02/072627 A2 | 9/2002 |
| WO | WO 2004/067023 A2 | 8/2004 |

OTHER PUBLICATIONS

Akatsuka, Y. et al., "Identification of a Polymorphic Gene, BCL2A1, Encoding Two Novel Hematopoietic Lineage-specific Minor Histocompatibility Antigens"; J. Exp. Med, The Rockefeller Univeristy Press, vol. 197, No. 11, pp. 1489-1500 (Jun. 2, 2003).

Andersen, M.H. et al., "Immunogenicity of Bcl-2 in patients with cancer"; Blood, vol. 105, No. 2 (Jan. 15, 2005).

Finnegan, NM. et al., "Induction of apoptosis in prostate carcinoma cells by BH3 peptides which inhibits Bak/Bcl-2 interactions"; British Journal of Cancer, vol. 85, No. 1, pp. 115-121 (2001).

Hirohashi, Y. et al., "An HLA-A24-restricted Cytotoxic T Lymphocyte Epitope of a Tumor-asociated Protein, Survivin"; Clinical Cancer Research, vol. 8, pp. 1731-1739 (Jun. 2002).

Lin, E.Y. et al., Characterization of A1, a Novel Hemopoietic-Specific Early-Response Gene with Sequence Similarity to bcl-2[1]; The Journal of Immunology, vol. 151, No. 4, pp. 1979-1988 (Aug. 15, 1993).

Nishida et al., Clinical relevance of a newly identified HLA-A24-restricted minor histocompatibility antigen epitope derived from BCL2A1, ASS-1, in patients receiving HLA genotypically matched unrelated bone marrow transplant; British Journal of Haematology, vol. 124, pp. 629-635 (2004).

Reed, J; "Bcl-2 family proteins"; Oncogene, 20, vol. 17, pp. 3225-3236 (1998).

Renkvist, N. et al., "A listing of human tumor antigens recognized by T cells"; Cancer Immunol Immunother, vol. 50, pp. 3-15 (2001).

Saeterdal, I. et al., "Frameshift-mutation-derived peptides as tumor-specific antigens in inherited and spontaneous colorectal cancer"; Proc Nat. Acad. Sci (USA), vol. 98, No. 23, pp. 13255-13260 (Nov. 6, 2001).

Schmidt, S.M. et al., "Survivin is a shared tumor-associated antigen expressed in a broad variety of malignancies and recognized by specific cytotoxic T cells"; Blood, vol. 102, No. 2 (Jul. 15, 2003).

Shangary, S. et al., "Recent advances in the development of anticancer agents targeting cell death inhibitors in the Bcl-2 protein family"; Lukemia, vol. 17, pp. 1470-1481 (2003).

Andersen, et al., "Regulators of apoptosis: suitable targets for immune therapy of cancer", Nature Reviews, Drug Discovery, vol. 4, No. 5, pp. 399-409, May 2005.

Andersen, et al., "Spontaneous Immunity Against Bcl-$x_L$ in Cancer Patients", Journal of Immunology, vol. 174, No. 4, pp. 2709-2714, Aug. 2005.

Sorensen, et al., "Efficient tumor cell lysis medicated by a Bcl-X(L) specific T cell clone isolated from a breast cancer patient", Cancer Immunology, Immunotherapy, vol. 56, No. 4, pp. 527-533, 2007.

\* cited by examiner

Primary Examiner—Misook Yu
(74) Attorney, Agent, or Firm—Iver P. Cooper

(57) ABSTRACT

The present invention relates to proteins belonging to the Bcl-2 family and peptides fragments thereof for use in pharmaceutical compositions. The disclosed proteins and peptide fragments are in particularly useful in vaccine compositions for treatment of cancer. The invention furthermore relates to methods of treatment using said compositions. It is also an aspect of the invention to provide T-cells and T-cell receptors specifically recognising the disclosed proteins and peptide fragments.

53 Claims, 12 Drawing Sheets

Figure 1:
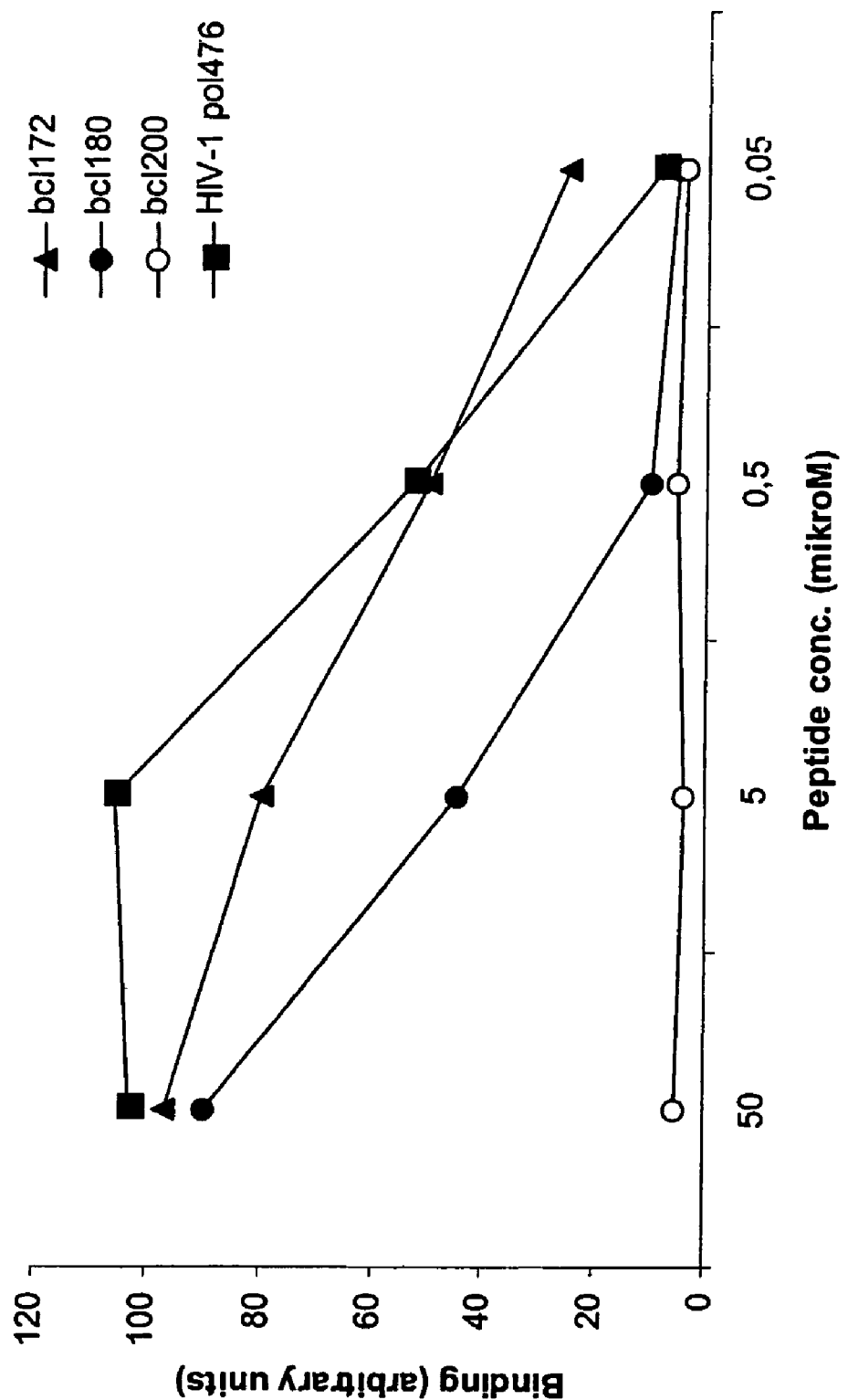

SEQUENCE LISTING

```
<160> NUMBER OF SEQ ID NOS: 64

<210> SEQ ID NO 1
<211> LENGTH: 9
<212> TYPE: PRT
<213> ORGANISM: artificial sequence
<220> FEATURE:
<223> OTHER INFORMATION: Peptide derived from Bcl-2

<400> SEQUENCE: 1

Ala Leu Val Gly Ala Cys Ile Thr Leu
1               5

<210> SEQ ID NO 2
<211> LENGTH: 9
<212> TYPE: PRT
<213> ORGANISM: artificial sequence
<220> FEATURE:
<223> OTHER INFORMATION: Peptide derived from Bcl-2

<400> SEQUENCE: 2

Ala Leu Ser Pro Val Pro Pro Val Val
1               5

<210> SEQ ID NO 3
<211> LENGTH: 9
<212> TYPE: PRT
<213> ORGANISM: artificial sequence
<220> FEATURE:
<223> OTHER INFORMATION: Peptide derived from Bcl-2

<400> SEQUENCE: 3

Ser Leu Ala Leu Val Gly Ala Cys Ile
1               5

<210> SEQ ID NO 4
<211> LENGTH: 9
<212> TYPE: PRT
<213> ORGANISM: artificial sequence
<220> FEATURE:
<223> OTHER INFORMATION: Peptide derived from Bcl-2

<400> SEQUENCE: 4

Lys Thr Leu Leu Ser Leu Ala Leu Val
1               5

<210> SEQ ID NO 5
<211> LENGTH: 9
<212> TYPE: PRT
<213> ORGANISM: artificial sequence
<220> FEATURE:
<223> OTHER INFORMATION: Peptide derived from Bcl-2

<400> SEQUENCE: 5

Leu Leu Ser Leu Ala Leu Val Gly Ala
1               5
```

```
<210> SEQ ID NO 6
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 6

Trp Leu Ser Leu Lys Thr Leu Leu Ser Leu
1               5                   10

<210> SEQ ID NO 7
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 7

Ala Ala Ala Gly Pro Ala Leu Ser Pro Val
1               5                   10

<210> SEQ ID NO 8
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 8

Pro Leu Phe Asp Phe Ser Trp Leu Ser Leu
1               5                   10

<210> SEQ ID NO 9
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 9

Phe Thr Ala Arg Gly Arg Phe Ala Thr Val
1               5                   10

<210> SEQ ID NO 10
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 10

Tyr Leu Asn Arg His Leu His Thr Trp Ile
1               5                   10

<210> SEQ ID NO 11
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 11

Asn Ile Ala Leu Trp Met Thr Glu Tyr Leu
1               5                   10
```

```
<210> SEQ ID NO 12
<211> LENGTH: 9
<212> TYPE: PRT
<213> ORGANISM: artificial sequence
<220> FEATURE:
<223> OTHER INFORMATION: Peptide derived from Survivin

<400> SEQUENCE: 12

Phe Leu Lys Leu Asp Arg Glu Arg Ala
1               5

<210> SEQ ID NO 13
<211> LENGTH: 10
<212> TYPE: PRT
<213> ORGANISM: artificial sequence
<220> FEATURE:
<223> OTHER INFORMATION: Peptide derived from Survivin

<400> SEQUENCE: 13

Thr Leu Pro Pro Ala Trp Gln Pro Phe Leu
1               5                   10

<210> SEQ ID NO 14
<211> LENGTH: 10
<212> TYPE: PRT
<213> ORGANISM: artificial sequence
<220> FEATURE:
<223> OTHER INFORMATION: Peptide derived from Survivin

<400> SEQUENCE: 14

Glu Leu Thr Leu Gly Glu Phe Leu Lys Leu
1               5                   10

<210> SEQ ID NO 15
<211> LENGTH: 9
<212> TYPE: PRT
<213> ORGANISM: artificial sequence
<220> FEATURE:
<223> OTHER INFORMATION: Modified survivin derived peptide

<400> SEQUENCE: 15

Leu Leu Leu Gly Glu Phe Leu Lys Leu
1               5

<210> SEQ ID NO 16
<211> LENGTH: 9
<212> TYPE: PRT
<213> ORGANISM: artificial sequence
<220> FEATURE:
<223> OTHER INFORMATION: Modified survivin derived peptide

<400> SEQUENCE: 16

Leu Met Leu Gly Glu Phe Leu Lys Leu
1               5

<210> SEQ ID NO 17
<211> LENGTH: 9
<212> TYPE: PRT
<213> ORGANISM: artificial sequence
<220> FEATURE:
<223> OTHER INFORMATION: Peptide derived from Survivin

<400> SEQUENCE: 17

Cys Pro Thr Glu Asn Glu Pro Asp Leu
1               5
```

```
<210> SEQ ID NO 18
<211> LENGTH: 9
<212> TYPE: PRT
<213> ORGANISM: artificial sequence
<220> FEATURE:
<223> OTHER INFORMATION: Peptide derived from Survivin

<400> SEQUENCE: 18

Glu Pro Asp Leu Ala Gln Cys Phe Phe
1               5

<210> SEQ ID NO 19
<211> LENGTH: 9
<212> TYPE: PRT
<213> ORGANISM: artificial sequence
<220> FEATURE:
<223> OTHER INFORMATION: Modified survivin derived peptide

<400> SEQUENCE: 19

Cys Pro Thr Glu Asn Glu Pro Asp Tyr
1               5

<210> SEQ ID NO 20
<211> LENGTH: 9
<212> TYPE: PRT
<213> ORGANISM: artificial sequence
<220> FEATURE:
<223> OTHER INFORMATION: Modified survivin derived peptide

<400> SEQUENCE: 20

Glu Pro Asp Leu Ala Gln Cys Phe Tyr
1               5

<210> SEQ ID NO 21
<211> LENGTH: 9
<212> TYPE: PRT
<213> ORGANISM: artificial sequence
<220> FEATURE:
<223> OTHER INFORMATION: Modified survivin derived peptide

<400> SEQUENCE: 21

Met Ala Glu Ala Gly Phe Ile His Tyr
1               5

<210> SEQ ID NO 22
<211> LENGTH: 10
<212> TYPE: PRT
<213> ORGANISM: artificial sequence
<220> FEATURE:
<223> OTHER INFORMATION: Modified survivin derived peptide

<400> SEQUENCE: 22

Pro Thr Glu Asn Glu Pro Asp Leu Ala Tyr
1               5                   10

<210> SEQ ID NO 23
<211> LENGTH: 10
<212> TYPE: PRT
<213> ORGANISM: artificial sequence
<220> FEATURE:
<223> OTHER INFORMATION: Peptide derived from Survivin

<400> SEQUENCE: 23

Gln Phe Glu Glu Leu Thr Leu Gly Glu Phe
1               5                   10

<210> SEQ ID NO 24
```

```
<211> LENGTH: 9
<212> TYPE: PRT
<213> ORGANISM: artificial sequence
<220> FEATURE:
<223> OTHER INFORMATION: Modified survivin derived peptide

<400> SEQUENCE: 24

Phe Thr Glu Leu Thr Leu Gly Glu Phe
1               5

<210> SEQ ID NO 25
<211> LENGTH: 10
<212> TYPE: PRT
<213> ORGANISM: artificial sequence
<220> FEATURE:
<223> OTHER INFORMATION: Modified survivin derived peptide

<400> SEQUENCE: 25

Arg Ile Ser Thr Phe Lys Asn Trp Pro Lys
1               5                   10

<210> SEQ ID NO 26
<211> LENGTH: 10
<212> TYPE: PRT
<213> ORGANISM: artificial sequence
<220> FEATURE:
<223> OTHER INFORMATION: Peptide derived from Survivin

<400> SEQUENCE: 26

Asp Leu Ala Gln Cys Phe Phe Cys Phe Lys
1               5                   10

<210> SEQ ID NO 27
<211> LENGTH: 11
<212> TYPE: PRT
<213> ORGANISM: artificial sequence
<220> FEATURE:
<223> OTHER INFORMATION: Peptide derived from Survivin

<400> SEQUENCE: 27

Arg Ile Ser Thr Phe Lys Asn Trp Pro Phe Leu
1               5                   10

<210> SEQ ID NO 28
<211> LENGTH: 10
<212> TYPE: PRT
<213> ORGANISM: artificial sequence
<220> FEATURE:
<223> OTHER INFORMATION: Peptide derived from ML-IAP

<400> SEQUENCE: 28

Arg Leu Gln Glu Glu Arg Thr Cys Lys Val
1               5                   10

<210> SEQ ID NO 29
<211> LENGTH: 10
<212> TYPE: PRT
<213> ORGANISM: artificial sequence
<220> FEATURE:
<223> OTHER INFORMATION: Peptide derived from ML-IAP

<400> SEQUENCE: 29

Gln Leu Cys Pro Ile Cys Arg Ala Pro Val
1               5                   10

<210> SEQ ID NO 30
<211> LENGTH: 10
```

```
<212> TYPE: PRT
<213> ORGANISM: Artificial sequence
<220> FEATURE:
<223> OTHER INFORMATION: Peptide derived from ML-IAP

<400> SEQUENCE: 30

Arg Leu Ala Ser Phe Tyr Asp Trp Pro Leu
1               5                   10

<210> SEQ ID NO 31
<211> LENGTH: 10
<212> TYPE: PRT
<213> ORGANISM: artificial sequence
<220> FEATURE:
<223> OTHER INFORMATION: Peptide derived from ML-IAP

<400> SEQUENCE: 31

Leu Leu Arg Ser Lys Gly Arg Asp Phe Val
1               5                   10

<210> SEQ ID NO 32
<211> LENGTH: 10
<212> TYPE: PRT
<213> ORGANISM: artificial sequence
<220> FEATURE:
<223> OTHER INFORMATION: Peptide derived from ML-IAP

<400> SEQUENCE: 32

Val Leu Glu Pro Pro Gly Ala Arg Asp Val
1               5                   10

<210> SEQ ID NO 33
<211> LENGTH: 10
<212> TYPE: PRT
<213> ORGANISM: artificial sequence
<220> FEATURE:
<223> OTHER INFORMATION: Peptide derived from ML-IAP

<400> SEQUENCE: 33

Pro Leu Thr Ala Glu Val Pro Pro Glu Leu
1               5                   10

<210> SEQ ID NO 34
<211> LENGTH: 9
<212> TYPE: PRT
<213> ORGANISM: artificial sequence
<220> FEATURE:
<223> OTHER INFORMATION: Peptide derived from ML-IAP

<400> SEQUENCE: 34

Ser Leu Gly Ser Pro Val Leu Gly Leu
1               5

<210> SEQ ID NO 35
<211> LENGTH: 9
<212> TYPE: PRT
<213> ORGANISM: artificial sequence
<220> FEATURE:
<223> OTHER INFORMATION: Peptide derived from ML-IAP

<400> SEQUENCE: 35

Gln Ile Leu Gly Gln Leu Arg Pro Leu
1               5

<210> SEQ ID NO 36
<211> LENGTH: 9
<212> TYPE: PRT
```

```
<213> ORGANISM: artificial sequence
<220> FEATURE:
<223> OTHER INFORMATION: Peptide derived from ML-IAP

<400> SEQUENCE: 36

Leu Thr Ala Glu Val Pro Pro Glu Leu
1               5

<210> SEQ ID NO 37
<211> LENGTH: 9
<212> TYPE: PRT
<213> ORGANISM: artificial sequence
<220> FEATURE:
<223> OTHER INFORMATION: Peptide derived from ML-IAP

<400> SEQUENCE: 37

Gly Met Gly Ser Glu Glu Leu Arg Leu
1               5

<210> SEQ ID NO 38
<211> LENGTH: 9
<212> TYPE: PRT
<213> ORGANISM: artificial sequence
<220> FEATURE:
<223> OTHER INFORMATION: Peptide derived from ML-IAP

<400> SEQUENCE: 38

Glu Leu Pro Thr Pro Arg Arg Glu Val
1               5

<210> SEQ ID NO 39
<211> LENGTH: 9
<212> TYPE: PRT
<213> ORGANISM: artificial sequence
<220> FEATURE:
<223> OTHER INFORMATION: Epitope from HIV-1 pol

<400> SEQUENCE: 39

Ile Leu Lys Glu Pro Val His Gly Val
1               5

<210> SEQ ID NO 40
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 40

Ser Leu Lys Thr Leu Leu Ser Leu Ala Leu
1               5                   10

<210> SEQ ID NO 41
<211> LENGTH: 10
<212> TYPE: PRT
<213> ORGANISM: artificial sequence
<220> FEATURE:
<223> OTHER INFORMATION: Peptide derived from Bcl-2

<400> SEQUENCE: 41

Glu Leu Tyr Gly Pro Ser Met Arg Pro Leu
1               5                   10

<210> SEQ ID NO 42
<211> LENGTH: 10
<212> TYPE: PRT
<213> ORGANISM: artificial sequence
```

-continued

```
<220> FEATURE:
<223> OTHER INFORMATION: Peptide derived from Bcl-XL

<400> SEQUENCE: 42

Tyr Leu Asn Asp His Leu Glu Pro Trp Ile
1               5                   10

<210> SEQ ID NO 43
<211> LENGTH: 9
<212> TYPE: PRT
<213> ORGANISM: artificial sequence
<220> FEATURE:
<223> OTHER INFORMATION: Peptide derived from Bcl-XL

<400> SEQUENCE: 43

Thr Ala Tyr Gln Ser Phe Glu Gln Val
1               5

<210> SEQ ID NO 44
<211> LENGTH: 9
<212> TYPE: PRT
<213> ORGANISM: artificial sequence
<220> FEATURE:
<223> OTHER INFORMATION: Peptide derived from Bcl-XL

<400> SEQUENCE: 44

Glu Met Gln Val Leu Val Ser Arg Ile
1               5

<210> SEQ ID NO 45
<211> LENGTH: 10
<212> TYPE: PRT
<213> ORGANISM: artificial sequence
<220> FEATURE:
<223> OTHER INFORMATION: Peptide derived from Bcl-XL

<400> SEQUENCE: 45

Arg Ile Ala Ala Trp Met Ala Thr Tyr Leu
1               5                   10

<210> SEQ ID NO 46
<211> LENGTH: 10
<212> TYPE: PRT
<213> ORGANISM: artificial sequence
<220> FEATURE:
<223> OTHER INFORMATION: Peptide derived from Bcl-XL

<400> SEQUENCE: 46

Trp Met Ala Thr Tyr Leu Asn Asp His Leu
1               5                   10

<210> SEQ ID NO 47
<211> LENGTH: 10
<212> TYPE: PRT
<213> ORGANISM: artificial sequence
<220> FEATURE:
<223> OTHER INFORMATION: Modified Bcl-2 peptide

<400> SEQUENCE: 47

Pro Leu Phe Asp Phe Ser Trp Val Ser Leu
1               5                   10

<210> SEQ ID NO 48
<211> LENGTH: 10
<212> TYPE: PRT
<213> ORGANISM: artificial sequence
<220> FEATURE:
```

<223> OTHER INFORMATION: Peptide derived from Bcl-XL

<400> SEQUENCE: 48

Val Leu Val Ser Arg Ile Ala Ala Trp Met
1               5                   10

<210> SEQ ID NO 49
<211> LENGTH: 10
<212> TYPE: PRT
<213> ORGANISM: artificial sequence
<220> FEATURE:
<223> OTHER INFORMATION: Peptide derived from Bcl-XL

<400> SEQUENCE: 49

Val Ala Phe Phe Ser Phe Gly Gly Ala Leu
1               5                   10

<210> SEQ ID NO 50
<211> LENGTH: 9
<212> TYPE: PRT
<213> ORGANISM: artificial sequence
<220> FEATURE:
<223> OTHER INFORMATION: Peptide derived from Bcl-XL

<400> SEQUENCE: 50

Arg Ile Ala Ala Trp Met Ala Thr Tyr
1               5

<210> SEQ ID NO 51
<211> LENGTH: 9
<212> TYPE: PRT
<213> ORGANISM: artificial sequence
<220> FEATURE:
<223> OTHER INFORMATION: Peptide derived from Bcl-XL

<400> SEQUENCE: 51

Ala Leu Cys Val Glu Ser Val Asp Lys
1               5

<210> SEQ ID NO 52
<211> LENGTH: 10
<212> TYPE: PRT
<213> ORGANISM: artificial sequence
<220> FEATURE:
<223> OTHER INFORMATION: Peptide derived from Mcl-1

<400> SEQUENCE: 52

Tyr Leu Arg Glu Gln Ala Thr Gly Ala Lys
1               5                   10

<210> SEQ ID NO 53
<211> LENGTH: 10
<212> TYPE: PRT
<213> ORGANISM: artificial sequence
<220> FEATURE:
<223> OTHER INFORMATION: Peptide derived from Mcl-1

<400> SEQUENCE: 53

Ser Ile Thr Asp Val Leu Val Arg Thr Lys
1               5                   10

<210> SEQ ID NO 54
<211> LENGTH: 10
<212> TYPE: PRT
<213> ORGANISM: artificial sequence
<220> FEATURE:
<223> OTHER INFORMATION: Peptide derived from Mcl-1

-continued

```
<400> SEQUENCE: 54

Leu Ile Ser Phe Gly Ala Phe Val Ala Lys
1               5                   10

<210> SEQ ID NO 55
<211> LENGTH: 9
<212> TYPE: PRT
<213> ORGANISM: artificial sequence
<220> FEATURE:
<223> OTHER INFORMATION: Peptide derived from Mcl-1

<400> SEQUENCE: 55

Arg Leu Leu Phe Phe Ala Pro Thr Arg
1               5

<210> SEQ ID NO 56
<211> LENGTH: 9
<212> TYPE: PRT
<213> ORGANISM: artificial sequence
<220> FEATURE:
<223> OTHER INFORMATION: Peptide derived from Mcl-1

<400> SEQUENCE: 56

Arg Thr Lys Arg Asp Trp Leu Val Lys
1               5

<210> SEQ ID NO 57
<211> LENGTH: 9
<212> TYPE: PRT
<213> ORGANISM: artificial sequence
<220> FEATURE:
<223> OTHER INFORMATION: Peptide derived from Mcl-1

<400> SEQUENCE: 57

Asp Ile Lys Asn Glu Asp Asp Val Lys
1               5

<210> SEQ ID NO 58
<211> LENGTH: 10
<212> TYPE: PRT
<213> ORGANISM: artificial sequence
<220> FEATURE:
<223> OTHER INFORMATION: Peptide derived from Mcl-1

<400> SEQUENCE: 58

Pro Ala Glu Glu Glu Glu Asp Asp Leu Tyr
1               5                   10

<210> SEQ ID NO 59
<211> LENGTH: 9
<212> TYPE: PRT
<213> ORGANISM: artificial sequence
<220> FEATURE:
<223> OTHER INFORMATION: Peptide derived from Mcl-1

<400> SEQUENCE: 59

Ser Pro Glu Glu Glu Leu Asp Gly Tyr
1               5

<210> SEQ ID NO 60
<211> LENGTH: 9
<212> TYPE: PRT
<213> ORGANISM: artificial sequence
<220> FEATURE:
<223> OTHER INFORMATION: Peptide derived from Mcl-1
```

```
<400> SEQUENCE: 60

Gln Ser Leu Glu Ile Ile Ser Arg Tyr
1               5

<210> SEQ ID NO 61
<211> LENGTH: 9
<212> TYPE: PRT
<213> ORGANISM: artificial sequence
<220> FEATURE:
<223> OTHER INFORMATION: Peptide derived from Mcl-1

<400> SEQUENCE: 61

Ala Gly Val Gly Ala Gly Leu Ala Tyr
1               5

<210> SEQ ID NO 62
<211> LENGTH: 9
<212> TYPE: PRT
<213> ORGANISM: artificial sequence
<220> FEATURE:
<223> OTHER INFORMATION: Modified Mcl-1 peptide

<400> SEQUENCE: 62

Arg Leu Lys Arg Asp Trp Leu Val Lys
1               5

<210> SEQ ID NO 63
<211> LENGTH: 9
<212> TYPE: PRT
<213> ORGANISM: artificial sequence
<220> FEATURE:
<223> OTHER INFORMATION: Modified Mcl-1 peptide

<400> SEQUENCE: 63

Gln Ser Asp Glu Ile Ile Ser Arg Tyr
1               5

<210> SEQ ID NO 64
<211> LENGTH: 9
<212> TYPE: PRT
<213> ORGANISM: artificial sequence
<220> FEATURE:
<223> OTHER INFORMATION: Modified Mcl-1 peptide

<400> SEQUENCE: 64

Gln Ser Glu Glu Ile Ile Ser Arg Tyr
1               5
```

PROTEINS BELONGING TO THE BCL-2 FAMILY AND FRAGMENTS THEREOF, AND THEIR USE IN CANCER PATIENTS

FIELD OF THE INVENTION

The present invention relates generally to the field of cancer prophylaxis and therapy. In particular there are provided isolated apoptosis regulating proteins or peptide fragments thereof that are capable of eliciting anti-cancer immune responses. Specifically, the use of such proteins belonging to the Bcl-2 protein family and immunogenic peptide fragments hereof in cancer treatment, diagnosis and prognosis is provided.

TECHNICAL BACKGROUND AND PRIOR ART

The development of resistance by cancer cells to a wide variety of chemotherapeutic agents poses a major obstacle in the successful treatment of cancer. Drug resistance is observed in a broad range of cancer cell types. Many mechanisms contribute to drug resistance, including drug inactivation, extrusion of the drug by cell membrane pumps, mutations of drug targets, and failure to initiate apoptosis. Prevention of apoptosis can result from a variety of conditions, including retention of the mitochondrial membrane potential and cytokine stimulation.

The search for proteins responsible for drug-resistant phenotypes has implicated the antiapoptotic molecule Bcl-2. Overexpression of Bcl-2 plays a role in the development of drug resistance in leukaemia and other apoptosis-prone tumours and, consequently, a poor prognosis in various human cancers. Bcl-2 belongs to a family of proteins, the Bcl-2 family, the members of which regulate apoptosis. The family includes both proapoptotic and antiapoptotic members. Although a precise understanding of how Bcl-2 exerts its antiapoptotic effects remains elusive, it has been found to be overexpressed in many cancers including lung, colorectal, prostate, and breast cancers as well as in leukaemia's and lymphomas.

Thus, Bcl-2 is a critical cellular factor, as increased expression levels of that protein confers resistance to apoptotic stimuli, thereby contributing to the pathogenesis and progression of cancer.

The process by which the mammalian immune system recognises and reacts to foreign or alien materials is a complex one. An important facet of the system is the T-cell response. This response requires that T cells recognise and interact with complexes of cell surface molecules referred to as human leukocyte antigens (HLA) constituting the human major histocompatibility complex (MHC), and peptides. The peptides are derived from larger molecules, which are processed by the cells, which in turn present the HLA/MHC molecule. The interaction of T cells and complexes of HLA/peptide is restricted, requiring a T cell that is specific for a particular combination of an HLA molecule and a peptide. If a specific T cell is not present, there is no T-cell response even if its partner complex is present. Similarly, there is no response if the specific complex is absent, but the T cell is present.

The mechanism by which T cells recognise cellular abnormalities has also been implicated in cancer. E.g. in WO92/20356, a family of genes is disclosed which are processed into peptides which, in turn, are expressed on cells surfaces, and can lead to lysis of the tumour cells by specific CTLs. These genes are referred to as the MAGE family and are said to code for "tumour rejection antigen precursors" or "TRAP" molecules, and the peptides derived therefrom are referred to as "tumour rejection antigens" or "TRAs".

In WO 94/05304, nonapeptides are disclosed which bind to the HLA-A1 molecule. This reference discloses that, given the known specificity of particular peptides for particular HLA molecules, one should expect a particular peptide to bind one HLA molecule, but not others. This is significant, as different individuals possess different HLA phenotypes. As a result, while identification of a particular peptide as being a partner for a specific HLA molecule has diagnostic and therapeutic ramifications, these are only relevant for individuals with that particular HLA phenotype.

Thus, it is well established that peptide epitopes derived from tumour associated antigens (TAAs) can be recognised as antigens by cytotoxic T lymphocytes (CTLs) in the context of MHC molecules. However, although it is generally accepted that most if not all, tumours are antigenic, only a few are indeed immunogenic in the sense that tumour progression is readily controlled by the immune system.

To overcome this limitation, several immunotherapeutic studies have been initiated, e.g. vaccinations with TAA-derived peptides. For melanoma, the tumour for which the largest number of CTL-defined TAAs has been characterised, powerful CTL responses against antigens have been induced by vaccination and some patients experienced a complete remission of their disease. However, most of the peptide epitopes used in these vaccination trials are melanocyte specific, and these peptides cannot be applied for tumours of non-melanocyte origin. Furthermore, expression of these TAAs is heterogeneous among tumours from different patients and can even vary among metastases obtained from one patient. However, during the last couple of years a number of tumour specific peptide antigens, which are expressed in a number of different cancers, have been identified, i.e. HER-2, Muc-1 and telomerase.

Apoptosis is a genetic program of cellular suicide, and inhibition of apoptosis has been suggested to be an important mechanism involved in cancer formation by extending the life span of cells favouring the accumulation of transforming mutations. Survivin is a recently identified member of the family of inhibitors of apoptosis proteins (IAPs). In a global gene expression analysis of about 4 million transcripts, survivin was identified as one of the top genes invariably up-regulated in many types of cancer but not in normal tissue. Solid malignancies overexpressing survivin include lung, colon, breast, pancreas, and prostate cancer as well as haematopoietic malignancies. Additionally, series of melanoma and non-melanoma skin cancers have been reported to be invariably survivin positive. The overexpression of survivin in most human cancers suggests a general role of apoptosis inhibition in tumour progression, a notion substantiated by the observation that in the case of colorectal and bladder cancer, as well as neuroblastoma, expression of survivin was associated with an unfavourable prognosis. In contrast, survivin is undetectable in normal adult tissues. These characteristics qualify survivin as a suitable TAA for both diagnostic and therapeutic purposes.

Thus, during the last decade a large number of TAAs have been identified which are recognised by CTLs in a major histocompatibility complex (MHC)-restricted fashion. As survivin is overexpressed in most human cancers and inhibition of its function results in increased apoptosis, this protein may serve as a target for therapeutic CTL responses.

The survivin protein and the potential diagnostic and therapeutic use hereof are disclosed in (1) and U.S. Pat. No. 6,245,523, which are incorporated herein by reference. Survivin is a 16.5 kDa cytoplasmic protein containing a single BIR and a highly charged carboxy-terminal coiled coil region instead of a RING finger, which inhibits apoptosis induced by growth factor (IL-3) withdrawal when transferred in B cell precursors. The gene coding for survivin is nearly identical to the sequence of Effector Cell Protease Receptor-1 (EPR-1), but oriented in the opposite direction, thus suggesting the existence of two separate genes duplicated in a head-to-head configuration. Accordingly, survivin can be described as an antisense EPR-1 product. Functionally, inhibition of survivin expression by up-regulating its natural antisense EPR-1 transcript results in massive apoptosis and decreased cell growth.

U.S. Pat. No. 6,245,523 discloses the isolation of purified survivin and it provides nucleic acid molecules that encode the survivin protein, and antibodies and other molecules that bind to survivin. U.S. Pat. No. 6,245,523 also discloses antiapoptotically active fragments of the survivin protein and variants hereof wherein an amino acid residue has been inserted N- or C-terminal to, or within, the disclosed survivin sequence. It is specifically disclosed that such peptides should contain key functional residues required for apoptosis, i.e. Trp at position 67, Pro at position 73 and Cys at position 84.

During the past decade numerous clinical trials have shown the feasibility of peptide specific vaccination to induce antitumor T-cell responses in cancer patients. The clinical course of the patients, however, was in most cases not improved. This discrepancy has in numerous cases been explained by immune escape mechanisms of the tumour cells. For therapeutic strategies targeting antigens that play an insignificant role in cancer growth, the selection of antigen deficient cancer cells is a well-recognised limitation.

In the case of breast cancer patients, however, a paradoxical role of Bcl-2 protein has been observed. In primary breast tumours Bcl-2 negativity has been associated with a worse clinical outcome. Additionally, it has been reported that overexpression of Bcl-2 protein is correlated with oestrogen receptor-positive tumours mediated by oestrogen receptor response elements in the promoter region of the Bcl-2 gene. The prognosis of oestrogen-positive tumours is more favourable than that of oestrogen receptor-negative tumours. Several possible explanations for these seemingly paradoxical results have been suggested, e.g. inhibitory effects of Bcl-2 on cell proliferation, regulation of Bcl-2 expression by oestrogen, and/or the presence of Bcl-2 antagonists that inhibit its cytoprotective function.

Still, the above studies also showed that overexpression of Bcl-2 in breast cancer is correlated with drug resistance, and that downregulation of Bcl-2 by antisense oligonucleotides modulates drug sensitivity in association with apoptosis. Furthermore, gene transfection of Bcl-2 into breast cancer cell lines has uniformly resulted in enhanced resistance to apoptosis. In addition, it has been described that the presence of another inhibitor of apoptosis, the protein survivin in breast carcinoma was strongly associated with expression of Bcl-2 and with reduced apoptotic index (AI) and poor overall survival. A similar association between survivin and Bcl-2 has been described in neuroblastoma, gastric cancer, colorectal cancer, and high-grade non-Hodgkin's lymphoma. Thus, in breast carcinoma as in most other human cancers, inhibition of apoptosis is a general feature, and expression of antiapoptosis genes, e.g. survivin and/or Bcl-2 genes, may cause more pronounced antiapoptotic effects, as reflected in reduced apoptotic index. Recently, is has been shown that survivin is a target for spontaneous T-cell reactivity in patients with various cancers. These initial findings have later been confirmed and strengthened (by ourselves and others).

SUMMARY OF THE INVENTION

The present invention is based on the discovery that MHC Class I restricted peptides can be derived from a different class of apoptosis regulating proteins than survivin, i.e. the Bcl-2 protein family, which are capable of binding to MHC Class I HLA molecules and thereby eliciting CTL immune responses in patients suffering cancer diseases. These findings demonstrate that proteins belonging to the Bcl-2 protein family acts as TRAP molecules, which are processed in vivo by cells into peptides having TRA functionality. These findings open the way for novel therapeutic and diagnostic approaches which may be generally applicable in the control of cancer diseases.

The present invention discloses that Bcl-2 is as a suitable target for immunotherapy against a range of cancer diseases. Bcl-2 is a critical cellular factor and its expression is of importance for the survival of tumour cells. Thus, Bcl-2 is an attractive target for vaccination because immune escape by down regulation or loss of expression of this protein would impair sustained tumour growth. Furthermore, in the studies leading to the present invention, the inventors searched for and detected spontaneous T-cell reactivity in PBL against Bcl-2 derived peptides in breast cancer patients using an ELISPOT assay.

Accordingly, the present invention pertains in a first aspect to an isolated protein belonging to the Bcl-2 protein family or an immunogenically active peptide fragment hereof for use as a medicament in the prevention or treatment of a cancer. In particular, the invention pertains to isolated immunogenically active peptide fragments derived from a protein belonging to the Bcl-2 protein family for use as a medicament in the prevention or treatment of a cancer.

In a further aspect, the invention provides a pharmaceutical composition comprising the above protein and/or peptide fragment of the invention.

It is also an aspect of the invention to provide a vaccine composition comprising an isolated protein belonging to the Bcl-2 protein family or an immunogenically active peptide fragment hereof or a nucleic acid encoding said protein or said peptide fragment for use as a medicament in the prevention or treatment of a cancer.

In still further aspects the invention relates to a diagnostic kit for ex vivo or in situ diagnosis of the presence in a cancer patient of T cells in PBLs or in tumor tissue that are reactive with a Bcl-2 protein family member, the kit comprising the peptide fragment of the invention as defined above; a complex of a peptide fragment of the invention and a Class I HLA molecule or a fragment of such molecule.

It is also an objective of the invention to provide a method of detecting in a cancer patient the presence of a Bcl-2 protein family member reactive T cells, the method comprising contacting a tumour tissue or a blood sample with a complex of the invention as defined above an detecting binding of the complex to the tissue or the blood cells.

Additionally, there is provided a molecule that is capable of binding specifically to a peptide fragment of the invention and a molecule that is capable of blocking such binding.

In another aspect the invention pertains to a method of treating a cancer disease, the method comprising administering to a patient suffering from the disease an effective amount of the pharmaceutical composition of the invention, the molecule of the invention that is capable of binding specifically to a peptide fragment of the invention and/or a molecule of the invention that is capable of blocking such binding.

In yet another aspect the invention provides the use of the protein or peptide fragment as defined herein in the manufacturing of a medicament for the treatment of a cancer disease.

DETAILED DISCLOSURE OF THE INVENTION

It is a major objective of the present invention to provide isolated proteins belonging to the Bcl-2 protein family or an immunologically active peptide fragment hereof for use as a medicament in the prevention or treatment of a cancer.

The Bcl-2 protein family includes several proteins, which regulate apoptosis. This family includes both proapoptoctic and antiapoptotic members. In the present specification the potential of this protein family as pharmaceutically or diagnostically active substances in cancer has been studied with particular reference to the Bcl-2 protein. In addition, the potential of Bcl-$X_L$ and Mcl-1 as pharmaceutically and diagnostically active substance is described in detail. However, it seems very likely that immune responses similar to those observed against the Bcl-2 protein or fragments hereof exist or can be introduced in cancer patients against other members of the Bcl-2 protein family, e.g. other antiapoptotic proteins such as Mcl-1 or Bcl-$X_L$, which are also related to drug resistance and over-expression in cancer. Accordingly, the invention pertains to any member of the Bcl-2 protein family, preferably any antiapoptotic member that is capable of eliciting immune responses in cancer patients, for example a protein selected from the group consisting of Bcl-2, Bcl-w, Mcl-1, Bfl-1/A1, Bcl-b, Bcl2-L-10 and Bcl-$X_L$, preferably selected from the group consisting of Bcl-2, Mcl-1, Bcl-w and Bcl-$X_L$, more preferably selected from the group consisting of Bcl-2, Mcl-1 and Bcl-$X_L$.

The Bcl-2 anti-apoptotic family members exert their oncogenic effects by inhibiting apoptosis in cells that are normally destined for death, thereby promoting the accumulation of cells in vivo.

All members of the Bcl-2 protein family contain at least one of four conserved motifs known as Bcl-2 homology (BH) domains (BH1, BH2, BH3, and BH4). In addition to the presence of BH domains, preferred antiapoptotic molecules possess a carboxyl-terminal membrane-anchoring domain (TM). Antiapoptotic members such as Bcl-2 and Bcl-$X_L$ contain all four BH domains, along with the transmembrane domain. Muitidomain proapoptotic proteins such as Bax and Bak contain all but the BH4 domain. A second subgroup of proapoptotic proteins, known as 'BH3-domain only' proteins (eg. Bad and Bid), consists of molecules that contain only the BH3 domain and lack other BH domains. Proapoptotic proteins such as Bcl-$X_S$ and Mcl-1S, representing alternatively spliced forms of the bcl-x and mcl-1 genes, respectively, lack BH1 and BH2 domains. Additionally, Mcl-1S lacks a transmembrane domain. Proteins belonging to the Bcl-2 family are for example described in ref. 6.

Even though it is preferred that the protein belonging to the Bcl-2 protein family has antiapoptotic properties, it is also comprised within the present invention that the protein belonging to the Bcl-2 family may be a proapoptotic protein, for example a protein selected from the group consisting of of Bax, Bok/Mtd, Bad, Bik/Nbk, Bid, Hrk/DP5, Bim, Noxa, Bmf and PUMA/bbc3.

In one preferred embodiment of the invention the protein belonging to the Bcl-2 protein family is Bcl-2, preferably human Bcl-2, more preferably Bcl-2 of the sequence with the primary accession number P10415 in the SwissProt database.

In another preferred embodiment of the invention the protein belonging to the Bcl-2 protein family is Bcl-$X_L$, preferably human Bcl-$X_L$, more preferably Bcl-$X_L$ of the sequence with the primary accession number Q07817 in the SwissProt database.

In yet another preferred embodiment of the invention the protein belonging to the Bcl-2 family is Mcl-1, preferably human Mcl-1, more preferably Mcl-1 of the sequence with the primary accession number Q07820 in the SwissProt database.

Since a number of human cancers express high levels of Bcl-2 and other members of the Bcl-2 family, immunotherapeutic strategies aiming at these antigens may have broad clinical applications. The major concern of such an approach would be the induction of auto-reactive immune responses. Thus, the future of vaccination based on members of this protein family will depend on both the therapeutic efficacy and on the type of side effects that may follow immunisation. When peptides derived from melanocyte differentiation antigens were first used to treat patients with stage IV melanoma it was envisioned that this might lead to pronounced destruction of melanocytes, which in turn would manifest itself clinically, e.g. as, vitiligo or retinitis. However, clinical experience demonstrated that the incidence of vitiligo in patients receiving vaccinations was not significantly higher than the incidence of melanoma associated hypopigmentation in patients receiving other forms of therapy. Additionally, no serious side-effects have been reported in various vaccination trials against self-antigens.

In one useful embodiment, there are provided novel MHC Class I-restricted peptide fragments (also referred to herein as "peptides") which are characterised by having at least one of several features, one of which is the ability to bind to the Class I HLA molecule to which it is restricted at an affinity as measured by the amount of the peptide that is capable of half maximal recovery of the Class I HLA molecule ($C_{50}$ value) which is at the most 50 µM as determined by the assembly binding assay as described herein. This assembly assay is carried out as described previously (2), and it is based on stabilisation of the HLA molecule after loading of peptide to the peptide transporter deficient cell line T2. Subsequently, correctly folded stable HLA heavy chains are immunoprecipitated using conformation dependent antibodies and the peptide binding is quantitated.

This assay provides a simple means of screening candidate peptides for their ability to bind to a given HLA allele molecule at the above affinity. In preferred embodiments, the peptide fragment of the invention in one having a $C_{50}$ value, which is at the most 30 µM, such as a $C_{50}$ value, which is at the most 20 µM including $C_{50}$ values of at the most 10 µM, at the most 5 µM and at the most 2 µM.

However, more preferred peptides according to the present invention are peptides capable of raising a specific T-cell response as determined by an ELISPOT assay, for example the ELISPOT assay described herein below in example 1, section 4. Some peptides although not binding MHC with high affinity still may give rise to a T-cell response as determined by ELISPOT. Other peptides capable of binding MHC with high affinity also gives rise to a T-cell response as determined by ELISPOT. Both kinds of peptides are preferred peptides according to the invention.

Hence, preferred peptides according to the present invention are peptides capable of raising a specific T-cell response as measured by an ELISPOT assay, wherein more than 50 peptide specific spots per $10^8$ cells, more preferably per $10^7$, even more preferably per $10^6$, yet more preferably per $10^5$ cells, such as per $10^4$ cells are measured.

As mentioned above, the HLA system represents the human major histocompatibility (MHC) system. Generally, MHC systems control a range of characteristics: transplantation antigens, thymus dependent immune responses, certain complement factors and predisposition for certain diseases. More specifically, the MHC codes for three different types of molecules, i.e. Class I, II and III molecules, which determine the more general characteristics of the MHC. Of these molecules, the Class I molecules are so-called HLA-A, HLA-B and HLA-C molecules that are presented on the surface of most nucleated cells and thrombocytes.

The peptides of the present invention are characterised by their ability to bind to (being restricted by) a particular MHC Class I HLA molecule. Thus, in one embodiment the peptide is one which is restricted by a MHC Class I HLA-A molecule including HLA-A1, HLA-A2, HLA-A3, HLA-A9, HLA-A10, HLA-A11, HLA-Aw19, HLA-A23(9), HLA-A24(9), HLA-A25(10), HLA-A26(10), HLA-A28, HLA-A29(w19), HLA-A30(w19), HLA-A31(w19), HLA-A32(w19), HLA-Aw33(w19), HLA-Aw34(10), HLA-Aw36, HLA-Aw43, HLA-Aw66(10), HLA-Aw68(28), HLA-A69(28). More simple designations are also used throughout the literature, where only the primary numeric designation is used, e.g. HLA-A19 or HLA-A24 instead of HLA-Aw19 and HLA-A24(49), respectively. In specific embodiments, the peptide of the invention is restricted a MHC Class I HLA species selected from the group consisting of HLA-A1, HLA-A2, HLA-A3, HLA-A11 and HLA-A24.

The peptides of the invention may e.g. be derived from known sequences of a Bcl-2 protein family member (3). In a preferred embodiment of the invention the peptide comprises (or more preferably consists of) at the most 200, preferably at the most 100, more preferably at the most 50, yet more preferably at the most 25, even more preferably at the most 20, yet even more preferably at the most 15, such as at the most 10, for example in the range of 9 to 10 contiguous amino acids of one of the above-mentioned members of the Bcl-2 protein family, preferably from Bcl-2 with primary accession no P10415, Mcl-1 with the primary accession no Q07820 or Bcl-$X_L$ with the primary accession no Q07817 in the SwissProt database.

The selection of peptides potentially having the ability to bind to a particular HLA molecule can be made by the alignment of known sequences that bind to a given particular HLA molecule to thereby reveal the predominance of a few related amino acids at particular positions in the peptides. Such predominant amino acid residues are also referred to herein as "anchor residues" or "anchor residue motifs". By following such a relatively simple procedure based on known sequence data that can be found in accessible databases, peptides can be derived from the Bcl-2 protein family molecule, which are likely to bind to the particular HLA molecule. Representative examples of such analyses for a range of HLA molecules are given in the below table:

| HLA allele | Position 1 | Position 2 | Position 3 | Position 5 | Position 6 | Position 7 | C-terminal |
|---|---|---|---|---|---|---|---|
| HLA-A1 |  | T, S | D, E |  |  | L | Y |
| HLA-A2 |  | L, M |  |  | V |  | L, V |
| HLA-A3 |  | L, V, M | F, Y |  |  |  | K, Y, F |
| HLA-A11 |  | V, I, F, Y | M, L, F, Y, I |  |  |  | K, R |
| HLA-A23 |  | I, Y |  |  |  |  | W, I |
| HLA-A24 |  | Y |  | I, V | F |  | I, L, F |
| HLA-A25 |  | M, A, T | I |  |  |  | W |
| HLA-A26 | E, D | V, T, I, L, F |  |  | I, L, V |  | Y, F |
| HLA-A28 | E, D | V, A, L |  |  |  |  | A, R |
| HLA-A29 |  | E |  |  |  |  | Y, L |
| HLA-A30 |  | Y, L, F, V |  |  |  |  | Y |
| HLA-A31 |  |  | L, M, F, Y |  |  |  | R |
| HLA-A32 |  | I, L |  |  |  |  | W |
| HLA-A33 |  | Y, I, L, V |  |  |  |  | R |
| HLA-A34 |  | V, L |  |  |  |  | R |
| HLA-A66 | E, D | T, V |  |  |  |  | R, K |
| HLA-A68 | E, D | T, V |  |  |  |  | R, K |
| HLA-A69 |  | V, T, A |  |  |  |  | V, L |
| HLA-A74 |  | T |  |  |  |  | V, L |
| HLA-B5 |  | A, P | F, Y |  |  |  | I, L |
| HLA-B7 | * | P |  |  |  |  | L, F |
| HLA-B8 |  |  | K |  | K, R |  | L |

-continued

| HLA allele | Position 1 | Position 2 | Position 3 | Position 5 | Position 6 | Position 7 | C-terminal |
|---|---|---|---|---|---|---|---|
| HLA-B14 | | R, K | | | | | L, V |
| HLA-B15 (B62) | | Q, L, K, P, H, V, I, M, S, T | | | | | F, Y, W |
| HLA-B17 | | | | | | | L, V |
| HLA-B27 | | R | | | | | Y, K, F, L |
| HLA-B35 | | P | | | | | I, L, M, Y |
| HLA-B37 | | D, E | | | | | I, L, M |
| HLA-B38 | | H | D, E | | | | F, L |
| HLA-B39 | | R, H | | | | | L, F |
| HLA-B40 (B60, 61) | | E | F, I, V | | | | L, V, A, W, M, T, R |
| HLA-B42 | | L, P | | | | | Y, L |
| HLA-B44 | | E | | | | | F, Y, W |
| HLA-B46 | | M, I, L, V | | | | | Y, F |
| HLA-B48 | | Q, K | | | | | L |
| HLA-B51 | | A, P, G | | | | | F, Y, I, V |
| HLA-B52 | | Q | F, Y | | | | I, V |
| HLA-B53 | | P | | | | | W, F, L |
| HLA-B54 | | P | | | | | |
| HLA-B55 | | P | | | | | A, V |
| HLA-B56 | | P | | | | | A, V |
| HLA-B57 | | A, T, S | | | | | F, W, Y |
| HLA-B58 | | A, T, S | | | | | F, W, Y |
| HLA-B67 | | P | | | | | L |
| HLA-B73 | | R | | | | | P |
| HLA-Cw1 | | A, L | | | | | L |
| HLA-Cw2 | | A, L | | | | | F, Y |
| HLA-Cw3 | | A, L | | | | | L, M |
| HLA-Cw4 | | Y, P, F | | | | | L, M, F, Y |
| HLA-Cw6 | | | | | | | L, I, V, Y |
| HLA-Cw6 | | Y | | | | | L, Y, F |
| HLA-Cw8 | | Y | | | | | L, I, |
| HLA-Cw16 | | A, L | | | | | L, V |

*In one embodiment there is no specific anchor residue for this position, however in a preferred embodiment the anchor residue is R or A.

Thus, as an example, nonapeptides potentially having the ability to bind to HLA-A1 would have one of the following sequences: Xaa-T-D-Xaa-Xaa-Xaa-L-Xaa-Y, Xaa-T-E-Xaa-Xaa-Xaa-L-Xaa-Y; Xaa-S-D-Xaa-Xaa-Xaa-L-Xaa-Y or Xaa-S-E-Xaa-Xaa-Xaa-L-Xaa-Y (Xaa indicating any amino acid residue). In a similar manner, sequences potentially having the ability to bind to any other HLA molecule can be designed.

It will be appreciated that the person of ordinary skill in the art will be able to identify further "anchor residue motifs" for a given HLA molecule.

Thus, in useful embodiments, the peptides of the invention include peptides, the sequences of which comprise, for each of the specific HLA alleles listed in the table, any of the amino acid residues as indicated in the table.

Thus, the peptides of the invention may be any of the above-mentioned peptides comprising contiguous sequences from Bcl-2 protein family members, wherein in the range of 1 to 10, preferably in the range of 1 to 5, more preferably in the range of 1 to 3, even more preferably in the range of 1 to 2, yet more preferably 1 amino acid has been exchanged for another amino acid, preferably in a manner so that the peptide comprises one or more, preferably all anchor residues of a given HLA-A specific peptide as indicated in the table above.

A non-limiting example of how to prepare peptides of Bcl-2 protein family members comprising anchor residues of a given HLA-A specific peptide is described in example 3 in the section "Modified peptide response". Thus, in one embodiment of the invention the peptide the peptide may be any peptide comprising at the most 200, preferably at the most 100, more preferably at the most 50, yet more preferably at the most 25, even more preferably at the most 20, yet more preferably at the most 15, even more preferably at the most 10 amino acids and comprising (or more preferably consisting of) a sequence selected from the group consisting of RLKRD-WLVK (SEQ ID NO:62), QSDEIISRY (SEQ ID NO:63) and QSEEIISRY (SEQ ID NO:64), more preferably selected from the group consisting of RLKRDWLVK (SEQ ID NO:62).

Thus, a simple approach to identify peptides of the invention includes the following steps: selecting a particular HLA molecule, e.g. one occurring at a high rate in a given population, carrying out an alignment analysis as described above to identify "anchor residue motifs" in the Bcl-2 protein family protein, isolating or constructing peptides of a suitable size that comprise one or more of the identified anchor residues and testing the resulting peptides for (i) capability to bind to the particular HLA molecule using the assembly assay as described herein, (ii) the capability of the peptides to elicit INF-γ-producing cells in a PBL population of a cancer patient at a frequency of at least 1 per $10^4$ PBLs as determined by an ELISPOT assay as described herein, and/or (iii) the capability of the peptides to detect in situ in a tumour tissue CTLs that are reactive with the epitope peptides being tested.

In specific embodiments, the peptide of the invention is an HLA-A2 restricted Bcl-2-derived peptide having a sequence selected from the following: ALVGACITL (SEQ ID NO:1), ALSPVPPVV (SEQ ID NO:2), SLALVGACI (SEQ ID NO:3), KTLLSLALV (SEQ ID NO:4), LLSLALVGA (SEQ ID NO:5), WLSLKTLLSL (SEQ ID NO:6), AAAGPALSPV (SEQ ID NO:7), PLFDFSWLSL (SEQ ID NO:8), FTARGR-FATV (SEQ ID NO:9), YLNRHLHTWI (SEQ ID NO:10), NIALWMTEYL (SEQ ID NO:11).

In one preferred embodiment the peptide may be any peptide consisting of at the most 200, preferably at the most 100, more preferably at the most 50, yet more preferably at the most 25, even more preferably at the most 20, yet more preferably at the most 15, even more preferably at the most 10 amino acids and comprising (or more preferably consisting of) a sequence selected from the group consisting of ALVGACITL (SEQ ID NO:1), ALSPVPPVV (SEQ ID NO:2), SLALVGACI (SEQ ID NO:3), KTLLSLALV (SEQ ID NO:4), LLSLALVGA (SEQ ID NO:5), WLSLKTLLSL (SEQ ID NO:6), AAAGPALSPV (SEQ ID NO:7), PLFDFSWLSL (SEQ ID NO:8), FTARGRFATV (SEQ ID NO:9), YLNRHLHTWI (SEQ ID NO:10), NIALWMTEYL (SEQ ID NO:11), more preferably selected from the group consisting of NIALWMTEYL (SEQ ID NO:11), YLNRHLHTWI (SEQ ID NO:10), PLFDFSWLSL (SEQ ID NO:8) and WLSLKTLLSL (SEQ ID NO:6), even more preferably selected from the group consisting of PLFDFSWLSL (SEQ ID NO:8) and WLSLKTLLSL (SEQ ID NO:6).

In another preferred embodiment the peptide may be any peptide consisting of at the most 200, preferably at the most 100, more preferably at the most 50, yet more preferably at the most 25, even more preferably at the most 20, yet more preferably at the most 15, even more preferably at the most 10 amino acids and comprising (or more preferably consisting of) a sequence selected from the group consisting of EMQV-LVSRI (SEQ ID NO:44), TAYQSFEQV (SEQ ID NO:43), YLNDHLEPWI (SEQ ID NO: 42), RIAAWMATYL (SEQ ID NO:45), WMATYLNDHL (SEQ ID NO:46), VLVSRI-AAWM (SEQ ID NO: 48) and VAFFSFGGAL (SEQ ID NO: 49), more preferably from the group consisting of TAYQS-FEQV (SEQ ID NO:43), YLNDHLEPWI (SEQ ID NO: 42), RIAAWMATYL (SEQ ID NO:45), WMATYLNDHL (SEQ ID NO:46), VLVSRIAAWM (SEQ ID NO: 48) and VAFFS-FGGAL (SEQ ID NO: 49), even more preferably selected from the group consisting of TAYQSFEQV (SEQ ID NO: 43), VAFFSFGGAL (SEQ ID NO: 49), VLVSRIAAWM (SEQ ID NO: 48) and RIAAWMATYL (SEQ ID NO:45) or selected from the group consisting of TAYQSFEQV (SEQ ID NO:43) and WMATYLNDHL (SEQ ID NO:46) or selected from the group consisting of YLNDHLEPWI (SEQ ID NO: 42).

In yet another preferred embodiment the peptide may be any peptide consisting of at the most 200, preferably at the most 100, more preferably at the most 50, yet more preferably at the most 25, even more preferably at the most 20, yet more preferably at the most 15, even more preferably at the most 10 amino acids and comprising (or more preferably consisting of) a sequence selected from the group consisting of RIAAW-MATY (SEQ ID NO:50) and ALCVESVDK (SEQ ID NO:51), more preferably selected from the group consisting of RIAAWMATY (SEQ ID NO:50).

In yet another preferred embodiment the peptide may be any peptide consisting of at the most 200, preferably at the most 100, more preferably at the most 50, yet more preferably at the most 25, even more preferably at the most 20, yet more preferably at the most 15, even more preferably at the most 10 amino acids and comprising (or more preferably consisting of) a sequence selected from the group consisting of YLREQATGAK (SEQ ID NO:52), SITDVLVRTK (SEQ ID NO 53), LISFGAFVAK (SEQ ID NO 54), RLLFFAPTR (SEQ ID NO:55), RTKRDWLVK (SEQ ID NO:56) and DIKNEDDVK (SEQ ID NO:57), more preferably selected from the group consisting of RLLFFAPTR (SEQ ID NO:55) and RTKRDWLVK (SEQ ID NO:56).

In yet another preferred embodiment the peptide may be any peptide consisting of at the most 200, preferably at the most 100, more preferably at the most 50, yet more preferably at the most 25, even more preferably at the most 20, yet more preferably at the most 15, even more preferably at the most 10 amino acids and comprising (or more preferably consisting of) a sequence selected from the group consisting of PAEEEEDDLY (SEQ ID NO:58), SPEEELDGY (SEQ ID NO:59), QSLEIISRY (SEQ ID NO:60) and AGVGAGLAY (SEQ ID NO:61), more preferably selected from the group consisting of PAEEEEDDLY (SEQ ID NO:58) and QSLEI-ISRY (SEQ ID NO:60).

In further useful embodiments, the peptide of the invention is a peptide, which is restricted by a MHC Class I HLA-B molecule including any of the following: HLA-B5, HLA-B7, HLA-B8, HLA-B12, HLA-B13, HLA-B14, HLA-B15, HLA-B16, HLA-B17, HLA-B18, HLA-B21, HLA-Bw22, HLA-B27, HLA-B35, HLA-B37, HLA-B38, HLA-B39, HLA-B40, HLA-Bw41, HLA-Bw42, HLA-B44, HLA-B45, HLA-Bw46 and HLA-Bw47. In specific embodiments, the MHC Class I HLA-B species to which the peptide of the invention is capable of binding is selected from HLA-B7, HLA-B35, HLA-B44, HLA-B8, HLA-B15, HLA-B27 and HLA-B51.

In further useful embodiments, the peptide of the invention is a peptide, which is restricted by a MHC Class I HLA-C molecule including any of the following: HLA-Cw1, HLA-Cw2, HLA-Cw3, HLA-Cw4, HLA-Cw5, HLA-Cw6, HLA-Cw7 and HLA-Cw1.

Preferably, the peptide fragment of the invention comprises less than 50 amino acid residues, and more preferably it comprises at the most 20 amino acid residues, such as at the most 10 amino acid residues. In specific embodiments, the peptide is a heptapeptide, an octopeptide, a nonapeptide, a decapeptide or an undecapeptide.

The peptide of the invention is, as mentioned above, derived from a Bcl-2 protein family member or a fragment hereof. The protein from which the peptide can be derived can be any Bcl-2 protein family member from any animal species in which the protein is expressed. In preferred embodiments, the starting protein is from a mammal species including a rodent species, rabbit and a primate species such as humans. Based on the sequence of the selected protein, the peptide of the invention is derived by any appropriate chemical or enzymatic treatment of the protein starting material that results in a peptide of a suitable size as indicated above, or it can be synthesised by any conventional peptide synthesis procedures with which the person of ordinary skills in the art is familiar.

The peptide of the invention may have a sequence which is a native sequence of the Bcl-2 protein family member from which is derived. However, peptides having a higher affinity to any given HLA molecule may be derived from such a native sequence by modifying the sequence by substituting, deleting or adding at least one amino acid residue, e.g. on the basis of the procedure described above whereby anchor residue motifs in respect of the given HLA molecule are identified.

A significant feature of the peptide of the invention is its capability to recognise or elicit INF-γ-producing responder T cells, i.e. cytotoxic T cells (CTLs) that specifically recognise the particular peptide in a PBL population or tumour cells of a cancer patient (target cells). This activity is readily determined by subjecting PBLs or tumour cells from a patient to an ELISPOT assay as described in reference (4) and in the following example. Prior to the assay, it may be advantageous to stimulate the PBL population or the tumour cells to be assayed by contacting the cells with the peptide to be tested. Preferably, the peptide is capable of eliciting or recognising INF-γ-producing T cells at a frequency of at least 1 per $10^4$ PBLs as determined by an ELISPOT assay as used herein. More preferably the frequency is at least 5 per $10^4$ PBLs, most preferably at least 10 per $10^4$ PBLs, such as at least 50 or 100 per $10^4$ PBLs.

The ELISPOT assay represents a strong tool to monitor Bcl-2 family-derived peptide specific T-cell responses. However, although it has been shown that ELISPOT reactivity in most cases correlates with the capacity of the CTLs to lyse target cells, the conclusive evidence for this notion can only be given directly. Therefore, a major implication of the findings herein is that the peptides of the invention may be expressed and complexed with HLA molecules on cancer cells. This renders these cancer cells susceptible to destruction by CTLs and emphasizes the potential usefulness of Bcl-2 family protein immunization to control the growth of neoplasms. The presence of spontaneous CTL-responses in PBLs from breast cancer patients to HLA-restricted Bcl-2-derived peptide epitopes substantiates the immunotherapeutic potential of these tumour antigens not only in breast cancer patients, but also, as Bcl-2 protein family member are overexpressed in many cancers including lung, colorectal, prostate cancers and in leukaemia and lymphomas, in a broad range of cancer diseases.

Accordingly, in another preferred embodiment the peptide of the invention is capable of eliciting INF-γ-producing cells in a PBL population of a patient having a cancer disease where a Bcl-2 protein family is expressed including a haematopoietic malignancy e.g chronic lymphatic leukaemia and chronic myeloid leukaemia, melanoma, breast cancer, cervix cancer, ovary cancer, lung cancer, colon cancer, pancreas cancer and prostate cancer.

In addition to their capacity to elicit immune responses in PBL populations it is also contemplated that the peptides of the invention are capable of eliciting cytolytic immune responses in situ, i.e. in solid tumour tissues. This may be demonstrated by providing HLA-peptide complexes, e.g. being multimerised and being provided with a detectable label, and using such complexes for immunohistochemistry stainings to detect in a tumour tissue CTLs that are reactive with the epitope peptide of the invention. Accordingly, a further significant feature of the peptide of the invention is that it is capable of in situ detection in a tumour tissue of CTLs that are reactive with the epitope peptide.

It is also contemplated that the peptides of the invention, in addition to their capacity to bind to HLA molecules resulting in the presentation of complexes of HLA and peptides on cell surfaces, which complexes in turn act as epitopes or targets for cytolytic T cells, may elicit other types of immune responses, such as B-cell responses resulting in the production of antibodies against the complexes and/or a Delayed Type Hypersensitivity (DTH) reaction. The latter type of immune response is defined as a redness and palpable induration at the site of injection of the peptide of the invention.

The vaccine composition according to the present invention may comprise a nucleic acid encoding a protein belonging to the Bcl-2 protein family or a peptide fragment thereof. Said nucleic acid may thus encode any of the above-mentioned proteins and peptide fragments. The nucleic acid may for example be DNA, RNA, LNA, HNA, PNA, preferably the nucleic acid is DNA or RNA.

The nucleic acids of the invention may be comprised within any suitable vector, such as an expression vector. Numerous vectors are available and the skilled person will be able to select a useful vector for the specific purpose. The vector may, for example, be in the form of a plasmid, cosmid, viral particle or artificial chromosome. The appropriate nucleic acid sequence may be inserted into the vector by a variety of procedures, for example, DNA may be inserted into an appropriate restriction endonuclease site(s) using techniques well known in the art. Apart from the nucleic acid sequence according to the invention, the vector may furthermore comprise one or more of a signal sequence, an origin of replication, one or more marker genes, an enhancer element, a promoter, and a transcription termination sequence. The vector may also comprise additional sequences. Construction of suitable vectors containing one or more of these components employs standard ligation techniques which are known to a person skilled in the art. The vector is preferably an expression vector, comprising the nucleic acid operably linked to a regulatory nucleic acid sequence directing expression thereof in a suitable cell. Within the scope of the present invention said regulatory nucleic acid sequence should in general be capable of directing expression in a mammalian cell, preferably a human cell, more preferably in an antigen presenting cell.

In one preferred embodiment the vector is a viral vector. Said viral vector may in addition to the nucleic acid encoding a Bcl-2 protein family member or peptide fragment thereof comprise a second nucleic acid sequence encoding a T-cell stimulatory polypeptide. The T-cell stimulatory polypeptide is preferably selected from the group consisting of B7.1, ICAM-1 and LFA-3.

The vector may also be a bacterial vector, such as an attenuated bacterial vector. Attenuated bacterial vectors may be used in order to induce lasting mucosal immune responses at the sites of infection and persistence. Different recombinant bacteria may be used as vectors, for example the bacterial vector may be selected from the group consisting of *Salmonella, Lactococcus]*, and *Listeria*. In general, induction of immunity to the heterologous antigen HPV16 L1 or E7 could be shown, with strong CTL induction and tumor regression in mice.

The invention also relates to a kit-of-parts comprising
i) any of the vaccine compositions described herein and/or
ii) any of the proteins belonging to the Bcl-2 protein family described herein and/or
iii) any of the peptide fragments of the proteins of ii) described herein and/or
iv) any of the nucleic acids encoding the proteins of ii) or the peptides of iii)
and a further anti-cancer agent.

The components of the kit-of-parts are preferably comprised in individual compositions, it is however comprised within the scope of the present invention that the components of the kit-of-parts all are comprised within the same composition. The components of the kit-of-parts may thus be administered simultaneously or sequentially in any order.

The anti-cancer agent may be an agent used in chemotherapy or gene therapy, immunostimulating substances or antibodies. The immunostimulating substances may for example be cytokines, such as cytokines selected from the group consisting of GM-CSF, type I IFN, interleukin 12 and interleukin 15. The antibody is preferably an immunestimulating antibody such as anti-CD40 or anti-CTLA4 antibodies. The immunestimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

It is evident that the findings of the present invention provide the basis for therapeutic as well as diagnostic applications of the protein or the peptide fragment of the invention.

Accordingly, in a further aspect the present invention provides a pharmaceutical composition comprising the protein or the peptide fragment of the invention, in particular a pharmaceutical composition which, when it is administered to a cancer patient, is capable of eliciting an immune response against the cancer disease including eliciting the production in the vaccinated patient of effector T cells having a cytotoxic effect against the cancer cells.

As it is well known, that the different HLA molecules are of different prevalence in the major human populations, there is a requirement of identifying peptide epitopes restricted to several HLA class I molecules to extend the patient cohort that can be treated according to the methods of the present invention. The characterisation of multiple Bcl-2 epitopes with different HLA restriction elements broadens the clinical potential of this target antigen in two important ways: (i) It increases the number of patients eligible for immunotherapy based on Bcl-2 derived peptides. The HLA-A2 antigen is expressed by around 50% of the Caucasian and Asian populations, the HLA-A1 and HLA-A3 antigens are both expressed by around 25% of Caucasians and 5% of Asians, whereas the HLA-A11 antigen is expressed by around 15% of Caucasians and 30% of Asians. Even though these numbers cannot be added up due to co-expression, a combination of peptides restricted by a multiplicity of these would certainly encompass most cancer patients, (ii) The collective targeting of several restriction elements in each patient is likely to decrease the risk of immune escape by HLA-allele loss. Loss of a single HLA allele is a significant component of MHC alterations described for cancer cells, whereas total loss of Class I expression is a rather infrequent event. Thus, with the identification of Bcl-2 epitopes restricted to different HLA alleles, it would be possible to target more than one HLA-molecule simultaneously in patients with allelic overlap.

Thus, it would be possible to develop highly immunogenic multi-epitope vaccines. Preferably, such vaccines should be designed so as to facilitate a simultaneous delivery of the best-suited Bcl-2-derived peptides optionally in combination with other suitable peptides and/or adjuvants as described hereinafter. The present invention encompasses such multi-epitope vaccines comprising Bcl-2-derived peptides optionally in combination with further proteins or peptides fragments not belonging to or derived from the Bcl-2 protein family and/or adjuvants as described hereinafter and/or clas II-MHC restricted epitopes as described below.

There has been an increased focus on eliciting tumor-specific T helper cell immunity, i.e., vaccinating with class II-MHC restricted epitopes despite the fact that tumors generally do not express class II MHC. This is based on the recent finding that the induction and efficacy of the vaccine-induced anti-tumor response in many cases requires the cooperation of tumor-specific CD4 positive $T_h$ cells. Thus, an important factor driving the development of vaccines having a more complex composition is the desire to target multiple tumor antigens e.g. by designing vaccines comprising or encoding a collection of carefully selected CTL and $T_h$ cell epitopes.

Obviously, multi-epitope vaccines constitute an efficient way to raise immunity against epitopes derived from several different antigens without the need for introducing (genes encoding) potentially hazardous proteins such as oncoproteins. Such vaccines also permit selective induction of immunity against subdominant and cryptic T cell epitopes, which can be especially important in the case of tumor-associated autoantigens for which tolerance may exist for the epitopes that are prominently presented in normal tissues. Furthermore, antigen-presenting cells may fail to present certain epitopes that are expressed on tumor cells because of functional differences between the immunoproteasomes of antigen-presenting cells and the 'constitutive' proteasomes present in most tumor cells. In the case of peptide-based vaccines, such epitopes can be administered in an 'MHC-ready' form, which enables presentation through exogenous loading independently of antigen uptake and processing by host antigen-presenting cells.

As the peptides of the invention are relatively small molecules it may be required in such compositions to combine the peptides with various materials such as adjuvants, to produce vaccines, immunogenic compositions, etc. Adjuvants, broadly defined, are substances which promote immune responses. Frequently, the adjuvant of choice is Freund's complete or incomplete adjuvant, or killed *B. pertussis* organisms, used e.g. in combination with alum precipitated antigen. A general discussion of adjuvants is provided in Goding, Monoclonal Antibodies: Principles & Practice (2nd edition, 1986) at pages 61-63. Goding notes, however, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. Recently, it has been proposed to use granulocyte-macrophage colony stimulating factor (GM-CSF), a well known cytokine, as an adjuvant (WO 97/28816).

The vaccine compositions according to the invention preferably comprise an adjuvant and/or a carrier. Examples of useful adjuvants and carriers are given herein below. Thus the protein belonging to the Bcl-2 protein family or peptide fragment thereof present in the composition can be associated with a carrier such as e.g. a protein or an antigen-presenting cell such as e.g. a dendritic cell (DC) capable of presenting to the Bcl-2 protein family or peptide fragment thereof to a T-cell.

Adjuvants are any substance whose admixture into the vaccine composition increases or otherwise modifies the immune response to the Bcl-2 protein family or peptide fragment thereof. Carriers are scaffold structures, for example a polypeptide or a polysaccharide, to which the Bcl-2 protein family or peptide fragment thereof is capable of being associated.

Adjuvants could for example be selected from the group consisting of: $AlK(SO_4)_2$, $AlNa(SO_4)_2$, $AlNH_4(SO_4)$, silica, alum, $Al(OH)_3$, $Ca_3(PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund's Complete Adjuvant (FCA), Freund's Incomplete Adjuvants, Merck Adjuvant 65, polynucleotides (for example, poly IC and poly AU acids), wax D from Mycobacterium, tuberculosis, substances found in Corynebacterium parvum, Bordetella pertussis, and members of the genus *Brucella*, liposomes or other lipid emulsions, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21. Preferred adjuvants to be used with the invention include oil/surfactant based adjuvants such as Montanide adjuvants (available from Seppic, Belgium), preferably Montanide ISA-51. Other preferred adjuvants are bacterial DNA based adjuvants, such as adjuvants including CpG oligonucleotide sequences. Yet other preferred adjuvants are viral dsRNA based adjuvants, such as poly I:C. Imidazochinilines are yet another example of preferred adjuvants. In addition, a preferred adjuvant is liposomes. The most preferred adjuvants are adjuvants suitable for human use.

Montanide adjuvants (all available from Seppic, Belgium), may be selected from the group consisting of Montanide ISA-51, Montanide ISA-50, Montanide ISA-70, Montanide ISA-206, Montanide ISA-25, Montanide ISA-720, Montanide ISA-708, Montanide ISA-763A, Montanide ISA-207, Montanide ISA-264, Montanide ISA-27, Montanide ISA-35, Montanide ISA 51F, Montanide ISA 016D and Montanide IMS, preferably from the group consisting of Montanide ISA-51, Montanide IMS and Montanide ISA-720, more preferably from the group consisting of Montanide ISA-51. Montanide ISA-51 (Seppic, Inc.) is oil/surfactant based adjuvants in which different surfactants are combined with either a non-metabolizable mineral oil, a metabolizable oil, or a mixture of the two. They are prepared for use as an emulsion with an aqueous solution comprising the protein belonging to the Bcl-2 protein family or peptide fragment thereof. The surfactant is mannide oleate. QS-21 (Antigenics; Aquila Biopharmaceuticals, Framingham, Mass.) is a highly purified, water-soluble saponin that handles as an aqueous solution. QS-21 and Montanide ISA-51 adjuvants can be provided in sterile, single-use vials.

A general discussion of adjuvants is provided in Goding, Monoclonal Antibodies: Principles & Practice (2nd edition, 1986) at pages 61-63. Goding notes, however, that when the antigen of interest is of low molecular weight, or is poorly immunogenic, coupling to an immunogenic carrier is recommended. Examples of such carrier molecules include keyhole limpet haemocyanin, bovine serum albumin, ovalbumin and fowl immunoglobulin. Various saponin extracts have also been suggested to be useful as adjuvants in immunogenic compositions. Recently, it has been proposed to use granulocyte-macrophage colony stimulating factor (GM-CSF), a well known cytokine, as an adjuvant (WO 97/28816).

Desirable functionalities of adjuvants capable of being used in accordance with the present invention are listed in the below table.

TABLE 1

Modes of adjuvant action

| Action | Adjuvant type | Benefit |
| --- | --- | --- |
| 1. Immunomodulation | Generally small molecules or proteins which modify the cytokine network | Upregulation of immune response. Selection of Th1 or Th2 |
| 2. Presentation | Generally amphipathic molecules or complexes which interact with immunogen in its native conformation | Increased neutralizing antibody response. Greater duration of response |
| 3. CTL induction | Particles which can bind or enclose immunogen and which can fuse with or disrupt | Cytosolic processing of protein yielding correct class 1 restricted peptides |

TABLE 1-continued

Modes of adjuvant action

| Action | Adjuvant type | Benefit |
|---|---|---|
| | cell membranes w/o emulsions for direct attachment of peptide to cell surface MHC-1 | Simple process if promiscuous peptide(s) known |
| 4. Targeting | Particulate adjuvants which bind immunogen. Adjuvants which saturate Kupffer cells | Efficient use of adjuvant and immunogen |
| | Carbohydrate adjuvants which target lectin receptors on macrophages and DCs | As above. May also determine type of response if targeting selective |
| 5. Depot Generation | w/o emulsion for short term Microspheres or nanospheres for long term | Efficiency Potential for single-dose vaccine |

Source: Cox, J. C., and Coulter, A. R. (1997). Vaccine 15, 248-56.

A vaccine composition according to the present invention may comprise more than one different adjuvant. Furthermore, the invention encompasses a therapeutic composition further comprising any adjuvant substance including any of the above or combinations thereof. It is also contemplated that the protein belonging to the Bcl-2 protein family or peptide fragments thereof, and the adjuvant can be administered separately in any appropriate sequence.

A carrier may be present independently of an adjuvant. The function of a carrier can for example be to increase the molecular weight of in particular peptide fragments in order to increase their activity or immunogenicity, to confer stability, to increase the biological activity, or to increase serum half-life. Furthermore, a carrier may aid presenting the protein belonging to the Bcl-2 family or peptide fragments thereof to T-cells. The carrier may be any suitable carrier known to the person skilled in the art, for example a protein or an antigen presenting cell. A carrier protein could be but is not limited to keyhole limpet hemocyanin, serum proteins such as transferrin, bovine serum albumin, human serum albumin, thyroglobulin or ovalbumin, immunoglobulins, or hormones, such as insulin or palmitic acid. For immunization of humans, the carrier must be a physiologically acceptable carrier acceptable to humans and safe. However, tetanus toxoid and/or diptheria toxoid are suitable carriers in one embodiment of the invention. Alternatively, the carrier may be dextrans for example sepharose.

Accordingly, the invention encompasses a therapeutic composition further comprising an adjuvant substance including any of the above or combinations thereof. It is also contemplated that the antigen, i.e. the peptide of the invention and the adjuvant can be administered simultaneously or separately in any appropriate sequence.

The choice of antigen in the pharmaceutical composition of the invention will depend on parameters determinable by the person of skill in the art. As it has been mentioned, each of the different peptides of the invention is presented on the cell surfaces by a particular HLA molecule. As such, if a subject to be treated is typed with respect to HLA phenotype, a peptide/peptides are selected that is/are known to bind to that particular HLA molecule.

Alternatively, the antigen of interest is selected based on the prevalence of the various HLA phenotypes in a given population. As an example, HLA-A2 is the most prevalent phenotype in the Caucasian population, and therefore, a composition containing a survivin derived peptide binding to HLA-A2 will be active in a large proportion of that population. However, the composition of the invention may also contain a combination of two or more survivin derived peptides, each interacting specifically with a different HLA molecule so as to cover a larger proportion of the target population. Thus, as examples, the pharmaceutical composition may contain a combination of a peptide restricted by a HLA-A molecule and a peptide restricted by a HLA-B molecule, e.g. including those HLA-A and HLA-B molecules that correspond to the prevalence of HLA phenotypes in the target population, such as e.g. HLA-A2 and HLA-B35. Additionally, the composition may comprise a peptide restricted by an HLA-C molecule.

It is contemplated that useful immunogenic compositions of the invention, in addition to a Bcl-2 protein family member derived peptide as defined herein may comprise an immunologically effective amount of the Bcl-2 protein family member as such as it is defined herein or an immunogenic fragment hereof.

The amount of the immunogenic peptide of the invention in the pharmaceutical composition may vary, depending on the particular application. However, a single dose of the immunogen is preferably anywhere from about 10 μg to about 5000 μg, more preferably from about 50 μg to about 2500 μg such as about 100 μg to about 1000 μg. Modes of administration include intradermal, subcutaneous and intravenous administration, implantation in the form of a time release formulation, etc. Any and all forms of administration known to the art are encompassed herein. Also any and all conventional dosage forms that are known in the art to be appropriate for formulating injectable immunogenic peptide composition are encompassed, such as lyophilised forms and solutions, suspensions or emulsion forms containing, if required, conventional pharmaceutically acceptable carriers, diluents, preservatives, adjuvants, buffer components, etc.

The pharmaceutical compositions may be prepared and administered using any conventional protocol known by a person skilled in the art. In example 5 a non-limiting example of preparation of a vaccine composition according to the invention is given as well as a non-limiting example of administration of such as a vaccine. It will be appreciated by the person skilled in the art that the protocol may be easily adapted to any of the vaccine compositions described herein.

In a further embodiment of the invention, the pharmaceutical composition of the invention is useful for treating a cancer patient, where, during cancer progression in that patient, the cancer cells have developed a reduced susceptibility to a chemotherapeutically active anti-cancer drug and/or radiotherapy.

The pharmaceutical composition of the invention may advantageously comprise at least one further immunogenic protein or peptide fragment hereof selected from a protein or peptide fragment not belonging to or derived from the Bcl-2 protein family, including a protein involved in regulation of cell apoptosis or a peptide fragment derived therefrom. As one example, such a further protein or peptide is survivin as defined above, or a peptide fragment hereof. In specific embodiments, a further immunogenic survivin-derived peptide is an HLA-A2 restricted peptide having a sequence selected from the following: FLKLDRERA (survivin$_{101-109}$) (SEQ ID NO:12), TLPPAWQPFL (survivin$_{5-14}$) (SEQ ID NO:13), ELTLGEFLKL (survivin$_{95-104}$) (SEQ ID NO:14), LLLGEFLKL (SEQ ID NO:15) and LMLGEFLKL (SEQ ID NO:16). (The designations in brackets indicate the positions of the residues in the survivin protein as disclosed in U.S. Pat. No. 6,245,523). LLLGEFLKL (SEQ ID NO:15) is a sequence derived from survivin$_{96-104}$ by substituting "T" in position 2 of the peptide with an "L" and LMLGEFLKL (SEQ ID NO:16) is derived from survivin$_{96-104}$ by substituting "T" in position 2 with "M". In further specific embodiments, the further immunogenic survivin-derived peptide is an HLA-B35-restricted survivin-derived peptide having a sequence selected from the following: CPTENEPDL (survivin$_{46-54}$) (SEQ ID NO:17), EPDLAQCFF (survivin$_{51-59}$) (SEQ ID NO:18), CPTENEPDY (SEQ ID NO:19) and EPDLAQCFY (SEQ ID NO:20). (The designations in brackets indicate the positions of the residues in the survivin protein as disclosed in U.S. Pat. No. 6,245,523). CPTENEPDY (SEQ ID NO:19) is a sequence derived from survivin46-54 by substituting "L" in the C-terminal of the peptide with a "Y" and EPDLAQCFY (SEQ ID NO:20) is derived from survivin$_{51-159}$ by substituting an "F" residue in the C-terminal 2 with a "Y".

In yet further embodiments, the further peptide is a HLA-A1 restricted peptide having a sequence selected from the following: Survivin$_{38-46}$ (Sur38Y9) (a C changed to a Y at P9, MAEAGFIHY)(SEQ ID NO:21), Survivin$_{47-56}$ (Sur47Y10) (a Q changed to a Y at P10, PTENEPDLAY(SEQ ID NO:22)), Survivin$_{92-101}$ (Sur92-101) (QFEELTLGEF) (SEQ ID NO:23), and Survivin$_{93-101}$ (Sur93T2 (a E changed to a T at P2, FTELTLGEF (SEQ ID NO:24)). The peptide of the invention may also be a HLA-A3 restricted peptide such as Survivin$_{18-24}$ (Sur18K10) (a F changed to a K at P10, RISTFKNWPK (SEQ ID NO:25) and/or a HLA-A11 restricted peptide such as Survivin$_{53-62}$ (Sur53-62) (DLAQCFFCFK) (SEQ ID NO:26) and/or a HLA-A2 restricted peptide such as Survivin$_{18-28}$ (Sur18-28) (RISTFKNWPFL)(SEQ ID NO:27).

However, in one preferred embodiment of the invention, the vaccine compositions do not comprise surviving or fragments thereof.

Other useful further peptides include the known apoptosis inhibitor polypeptide ML-IAP which has a rather selective expression, and is detected in melanomas. Thus, fragments of ML-IAP capable of eliciting a specific T-cell response i.e. a cytotoxic T-cell response or a helper T-cell response may optionally be included in the composition of the present invention. Useful peptide fragments of ML-IAP include any of the ML-IAP fragments described in patent application WO2004/089980, which is hereby incorporated by reference in its entirety, preferably ML-IAP$_{245}$ (RLQEERTCKV)(SEQ ID NO:28), ML-IAP$_{280}$ (QLCPICRAPV)(SEQ ID NO:29), ML-IAP$_{90}$ (RLASFYDWPL)(SEQ ID NO:30), ML-IAP$_{154}$ (LLRSKGRDFV)(SEQ ID NO:31), ML-IAP$_{230}$ (VLEPPGARDV)(SEQ ID NO:32), ML-IAP$_{98}$ (PLTAEVPPEL) (SEQ ID NO:33), ML-IAP$_{34}$ (SLGSPVLGL) (SEQ ID NO:34) ML-IAP$_{54}$ (QILGQLRPL)(SEQ ID NO:35), ML-IAP$_{99}$ (LTAEVPPEL)(SEQ ID NO:36), ML-IAP$_{83}$ (GMGSEELRL)(SEQ ID NO:37) and ML-IAP$_{200}$ (ELPTPRREV) (SEQ ID NO:38).

Other useful further peptides include TRAG-3 and peptide fragments thereof. TRAG-3 exist in at least two alternatively spliced forms and peptides of all TRAG-3 splice forms are useful as further peptides. In particular, fragments of any TRAG-3 splice form, wherein said fragments are capable of eliciting a specific T-cell response i.e. a cytotoxic T-cell response or a helper T-cell response may optionally be included in the composition of the present invention.

Additionally, the composition according to the present invention may be provided as a multiepitope vaccine comprising class I restricted epitope and class II restricted epitopes as defined hereinbefore.

The immunoprotective effect of the composition of the invention can be determined using several approaches e.g. as described in WO 97/28816, supra. A successful immune response may also be determined by the occurrence of DTH reactions after immunisation and/or the detection of antibodies specifically recognising the peptide(s) of the vaccine composition.

In preferred embodiments, the pharmaceutical composition of the invention is a vaccine composition. The pharmaceutical composition may thus be an immunogenic composition or vaccine capable of eliciting an immune response to a cancer disease. As used herein, the expression "immunogenic composition or vaccine" refers to a composition eliciting at least one type of immune response directed against cancer cells. Thus, such an immune response may be any of the types mentioned above: A CTL response where CTLs are generated that are capable of recognising the HLA/peptide complex presented on cell surfaces resulting in cell lysis, i.e. the vaccine elicits the production in the vaccinated subject of effector T-cells having a cytotoxic effect against the cancer cells; a B-cell response giving rise to the production of anti-cancer antibodies; and/or a DTH type of immune response.

In useful embodiments an immunogenic response directed against a cancer disease is elicited by administering the peptide of the invention either by loading MHC class I molecules on antigen presenting cells (APCs) from the patient, by isolating PBLs from the patient and incubating the cells with the peptide prior to injecting the cells back into the patient or by isolating precursor APCs from the patient and differentiating the cells into professional APCs using cytokines and antigen before injecting the cells back into the patient.

It is thus an aspect of the invention to provide vaccine compositions comprising antigen presenting cells comprising a protein belonging to the Bcl-2 family or a peptide fragment thereof or a nucleic acid encoding said protein or said peptide fragment. The antigen presenting cell may be any cell capable of presenting an antigen to a T-cell. Preferred antigen presenting cells are dendritic cells. The dendritic cells (DC) may be prepared and used in therapeutic procedure according to any suitable protocol, for example as described herein below. It will be appreciated by the person skilled in the art that the protocol may be adopted to use with patients with different HLA type and different diseases.

Dendritic cells (DC) are pulsed with 50 µg/ml HLA-restricted peptide (synthesized at GMP quality) for 1 h at 37° C. peptide and 5×10$^6$ cells are administered subcutaneously at day 1 and 14, subsequently every 4 weeks, additional leukapheresis after 5 vaccinations. The generation of DC for clinical use and quality control can be performed essentially as described in ref. 5.

Thus, in one embodiment of the present invention, a method for treating cancer patients is one wherein the peptide is administered by presenting the peptide to the patient's antigen presenting cells (APCs) ex vivo followed by injecting the thus treated APCs back into the patient. There are at least two alternative ways of performing this. One alternative is to isolate APCs from the cancer patient and incubate (load) the MHC class I molecules with the peptide. Loading the MHC class I molecules means incubating the APCs with the peptide so that the APCs with MHC class I molecules specific for the peptide will bind the peptide and therefore be able to present it to T cells. Subsequently, the APCs are re-injected into the patient. Another alternative way relies on the recent discoveries made in the field of dendritic cell biology. In this case, monocytes (being dendritic cell precursors) are isolated from the patient and differentiated in vitro into professional APC (or dendritic cells) by use of cytokines and antigen. Subsequently, the in vitro generated DCs are pulsed with the peptide and injected into the patient.

Due to the fact that members of the Bcl-2 protein family appear to be expressed in a range of cancer forms, it is very likely that vaccines of the invention can be provided to control any type of cancer disease where such proteins are expressed. Thus, as examples, the vaccine composition of the invention is immunologically active against a haematopoietic malignancy including chronic lymphatic leukemia and chronic myeloid leukaemia, melanoma, breast cancer, cervix cancer, ovary cancer, lung cancer, colon cancer, pancreas cancer and prostate cancer.

From the above description, the skilled person will readily realise that the proteins and/or peptides of the invention are useful as cancer diagnostic tools. Therefore, the peptides of the invention provide the basis for developing widely applicable diagnostic and prognostic procedures in respect of cancer diseases. Thus, in other useful embodiments the composition of the invention is a composition for ex vivo or in situ diagnosis of the presence in a cancer patient, e.g. based on the detection of Bcl-2 protein family member reactive T cells among PBLs or in tumour tissue.

Accordingly, there is, in still further aspects, provided a diagnostic kit for ex vivo or in situ diagnosis of the presence in a cancer patient of Bcl-2 family member reactive T cells among PBLs or in tumour tissue comprising one or more peptides of the invention, and a method of detecting in a cancer patient the presence of such reactive T cells, the method comprising contacting a tumour tissue or a blood sample with a complex of a peptide of the invention and a Class I HLA molecule or a fragment of such molecule and detecting binding of the complex to the tissue or the blood cells.

Another useful diagnostic or prognostic approach is based on generating antibodies in a heterologous animal species, e.g. murine antibodies directed against a human Bcl-2 protein family member-derived peptide of the invention, which can then be used, e.g. to diagnose for the presence of cancer cells presenting the peptide. For such immunisation purposes, the amount of peptide may be less than that used in the course of in vivo therapy, such as that mentioned above. In general, a preferred dose can range from about 1 µg to about 750 µg of peptide. It is also possible to produce monoclonal antibodies based on immunisation with a peptide of the invention. Accordingly, the present invention also relates to a molecule, in particular a monoclonal or polyclonal antibody including a fragment hereof, that is capable of binding specifically to a peptide of the invention and to a molecule that is capable of blocking such a binding, e.g. an antibody raised against the monoclonal or polyclonal antibody directed against a peptide of the invention. The invention furthermore relates to isolated T-cell receptors capable of binding specifically to a peptide or a protein of the invention as well as to isolated nucleic acids encoding same. Such T-cell receptors may for example be cloned from protein or peptide specific T-cells using standard techniques well known to the skilled person.

In one aspect the invention also relates to isolated T-cells comprising T-cell receptors capable of binding specifically to any of the proteins belonging to the Bcl-2 family and/or peptide fragments thereof described herein. The isolated T-cells are preferably T-cells that have been expanded in vitro. Methods of expanding T-cells in vitro are well known to the skilled person. Such T-cells may in particular be useful in the treatment of cancer by adaptive transfer or autologous cell transfer. Thus, the invention also relates to methods of treatment comprising administering T-cells comprising T-cell receptors capable of binding specifically to a protein belonging to the Bcl-2 family or peptide fragments thereof to an individual, such as a human being suffering from cancer. The invention furthermore relates to use of T-cells comprising T-cell receptors capable of binding specifically to a protein belonging to the Bcl-2 family or peptide fragments thereof for the preparation of a medicament for the treatment of cancer. Autologous cell transfer may be performed essentially as described in ref. 7.

In one aspect, the invention provides a complex of a peptide of the invention and a Class I HLA molecule or a fragment of such molecule, which is useful as a diagnostic reagent such as it is described supra. Such a complex may be monomeric or multimeric.

The present invention provides the means for alleviating or curing a cancer disease. Accordingly, it is a further aspect of the invention to provide a method of treating a cancer disease associated with the expression of a Bcl-2 protein family member, including as examples: a haematopoietic malignancy including chronic lymphatic leukaemia and chronic myeloid leukaemia, melanoma, breast cancer, cervix cancer, ovary cancer, lung cancer, colon cancer, pancreas cancer and prostate cancer, which method comprises administering to a patient suffering from the disease an effective amount of the pharmaceutical composition according to the invention, a molecule that is capable of binding specifically to a peptide of the invention and/or a molecule that is capable of blocking the binding of such a molecule.

In some cases it will be appropriate to combine the treatment method of the invention with a conventional cancer treatment such as chemotherapy, radiotheraphy, treatment with immunostimulating substances, gene therapy, treatment with antibodies and treatment using dendritic cells. Since elevated expression of Bcl-2 protein family members in tumour cells is correlated with drug resistance, the combination of a Bcl-2-based immunotherapy as disclosed by the present invention with cytotoxic chemotherapy might be an effective approach to treat cancer.

In one aspect the invention relates to methods of monitoring immunisation, said method comprising the steps of
  i) providing a blood sample from an individual
  ii) providing a protein belonging to the Bcl-2 protein family or a peptide fragment hereof, wherein said protein or peptide may be any of the proteins or peptides described herein
  iii) determining whether said blood sample comprises antibodies or T-cells comprising T-cell receptors specifically binding the protein or peptide iv) thereby determining whether an immune response to said protein or peptide has been raised in said individual.

The individual is preferably a human being, for example a human being that has been immunised with a protein belonging to the Bcl-2 protein family or a peptide fragment hereof or a nucleic acid encoding said protein or peptide.

Figure 2:
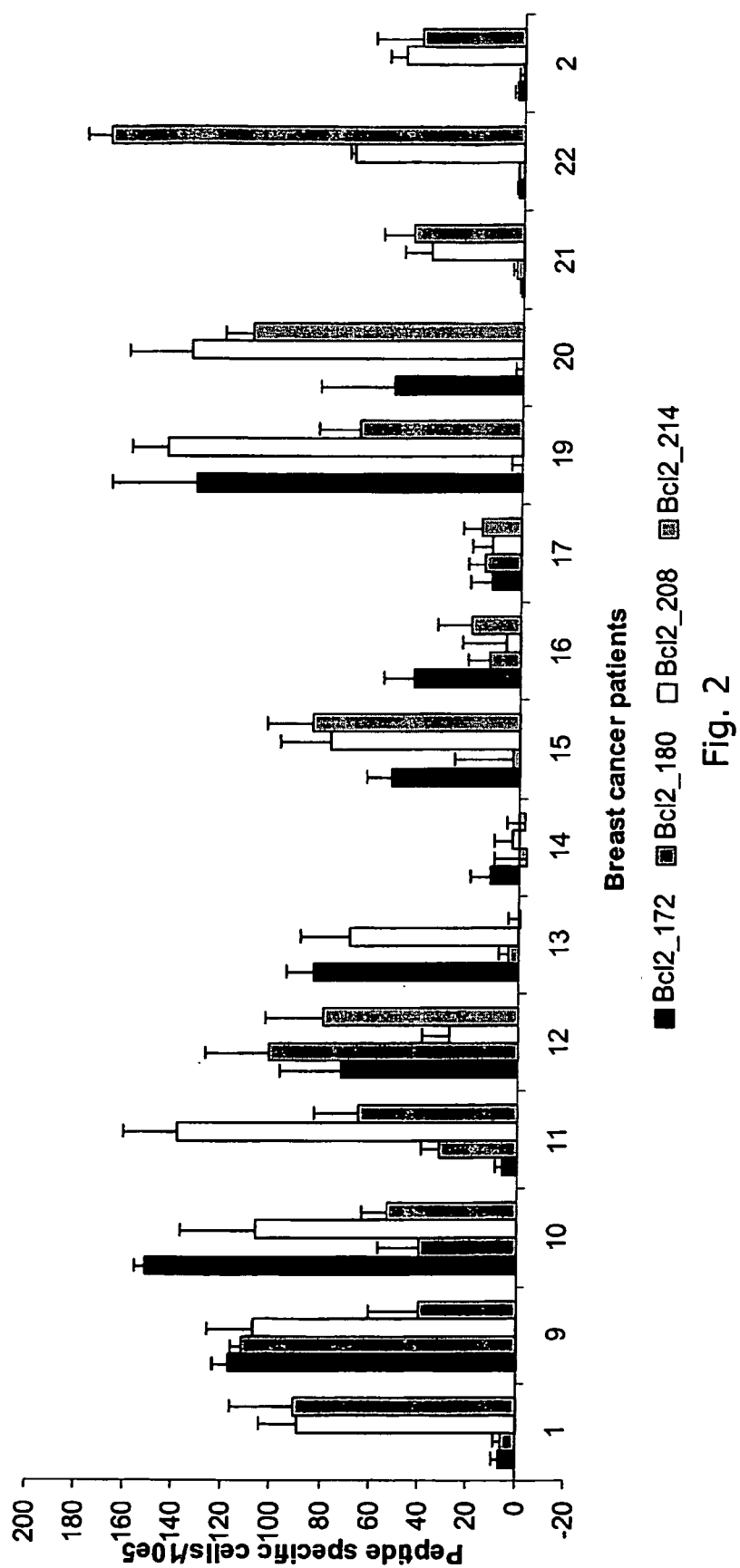

The invention will now be illustrated by the following, non-limiting examples and the drawings wherein FIG. 1 shows identification of HLA-A2 binding peptides from Bcl-2. Class I MHC heavy chain bands were quantified using a Phosphorimager. The amount of stabilised HLA-A2 heavy chain is directly related to the binding affinity of the added peptide. The binding of the HLA-A2-restricted positive control peptide HIV Pol$_{476}$ (black square) was compared with the peptides Bcl$_{172}$ (black triangle), Bcl$_{180}$ (black circle), and Bcl$_{200}$ (white circle) and FIG. 2 illustrates T-cell response against the peptides Bcl$_{172}$, Bcl$_{180}$, Bcl$_{208}$, and Bcl$_{214}$. PBL from 15 breast cancer patients were analysed. T-lymphocytes were stimulated once with peptide before plated at $10^5$ cells per well in triplicates either without or with peptide. The average number of peptide specific spots (after subtraction of spots without added peptide) was calculated for each patient using the ImmunoSpot® Series 2.0 Analyzer (CTL Analyzers, LLC, Cleveland, US).

Figure 3:
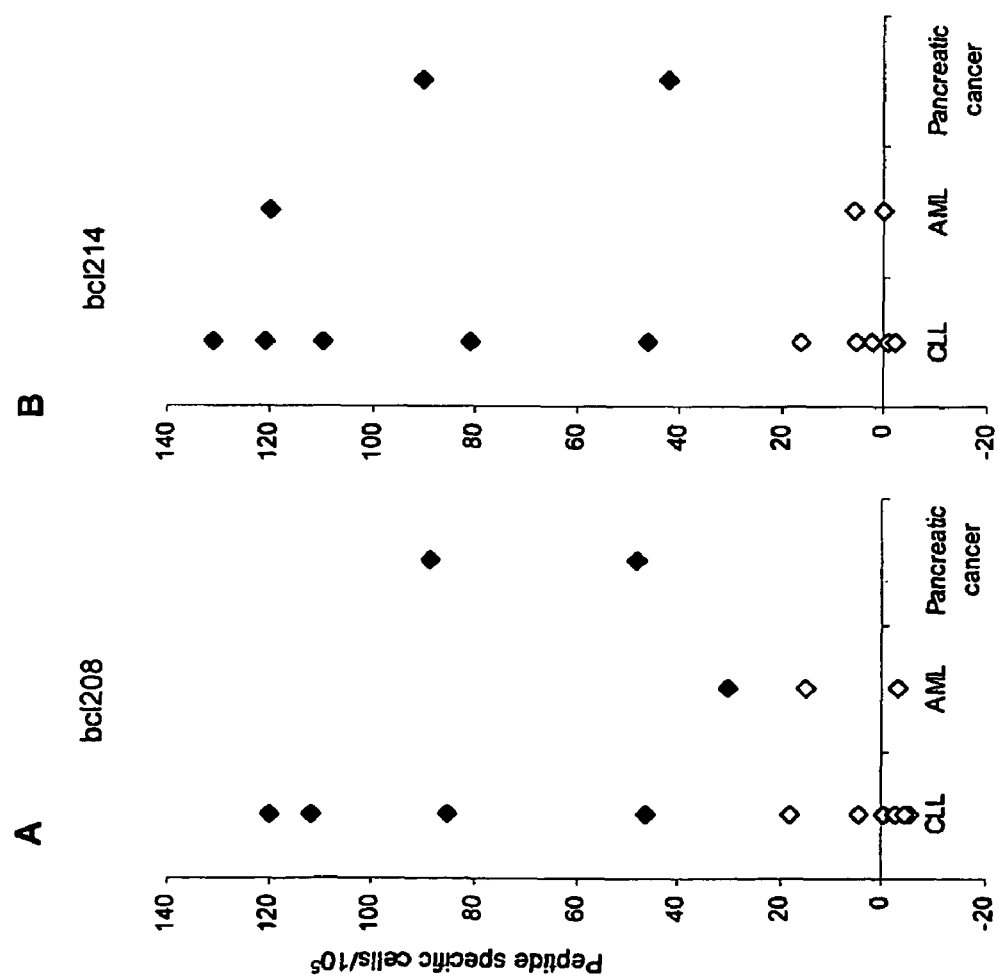

FIG. 3 illustrates T-cell responses against Bcl-2 as measured by INF-☐ ELISPOT. PBL from ten HLA-A2 positive CLL patients, three HLA-A2 positive AML patients and two Pancreatic cancer patients (PC) were analyzed. The peptides Bcl$_{208}$ (A) and Bcl$_{214}$ (B) were examined. T-lymphocytes were stimulated once with peptide before plated at $10^5$ cells per well in triplicates either without or with peptide. The average number of peptide specific spots (after subtraction of spots without added peptide) was calculated for each patient using the ImmunoSpot® Series 2.0 Analyzer (CTL Analyzers, LLC, Cleveland, US). Responders (defined as average number of antigen specific spots±½ standard deviation>25 per $10^5$ lymphocytes) are marked as black squares, whereas non-responding individuals are marked as white squares.

Figure 4:
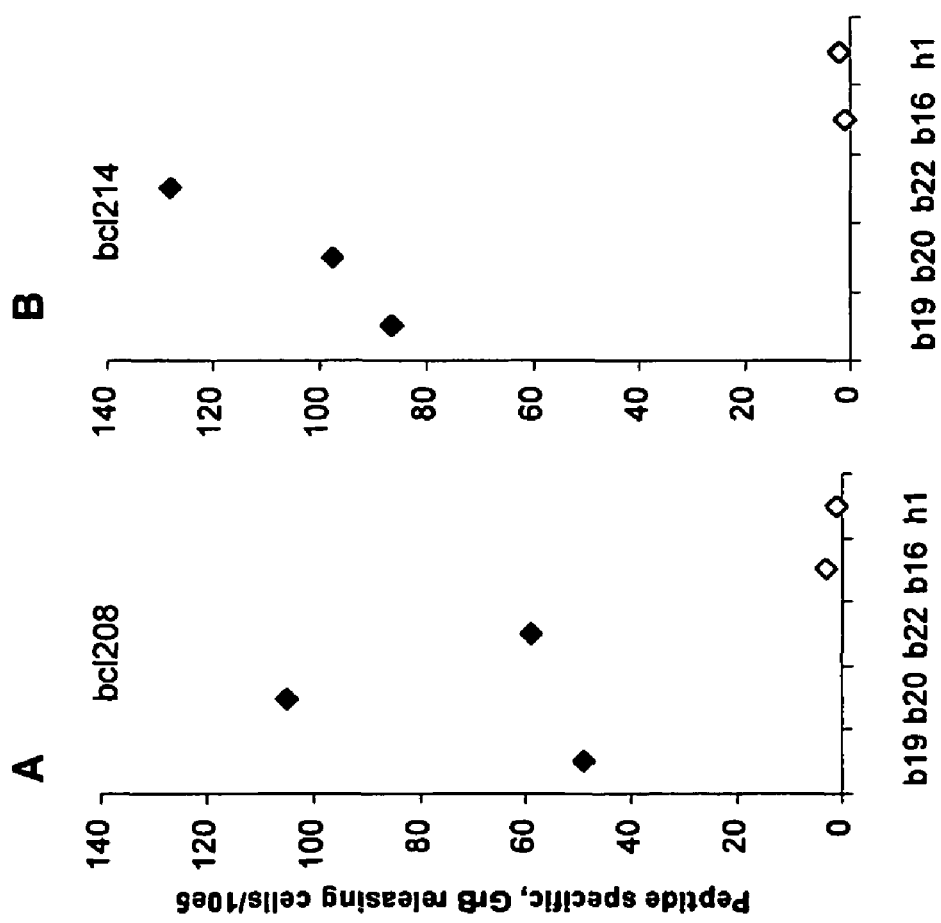

FIG. 4 illustrates detection of Bcl-2 specific CTL by granzyme B ELISPOT. T-lymphocytes from four different late stage breast cancer patients (b19, b20, b22, b16) and a healthy controls (h1) were stimulated once with peptide before plated at $10^5$ cells per well in triplicates either without or with peptide Bcl$_{208}$ (A) or Bcl$_{214}$ (B). The average number of peptide specific Granzyme B spots (after subtraction of spots without added peptide) was calculated for each patient using the ImmunoSpot® Series 2.0 Analyzer (CTL Analyzers, LLC, Cleveland, US). Responders (defined as average number of antigen specific spots±½ standard deviation>25 per $10^5$ lymphocytes) are marked as black squares, whereas non-responding individuals are marked as white squares.

Figure 5:
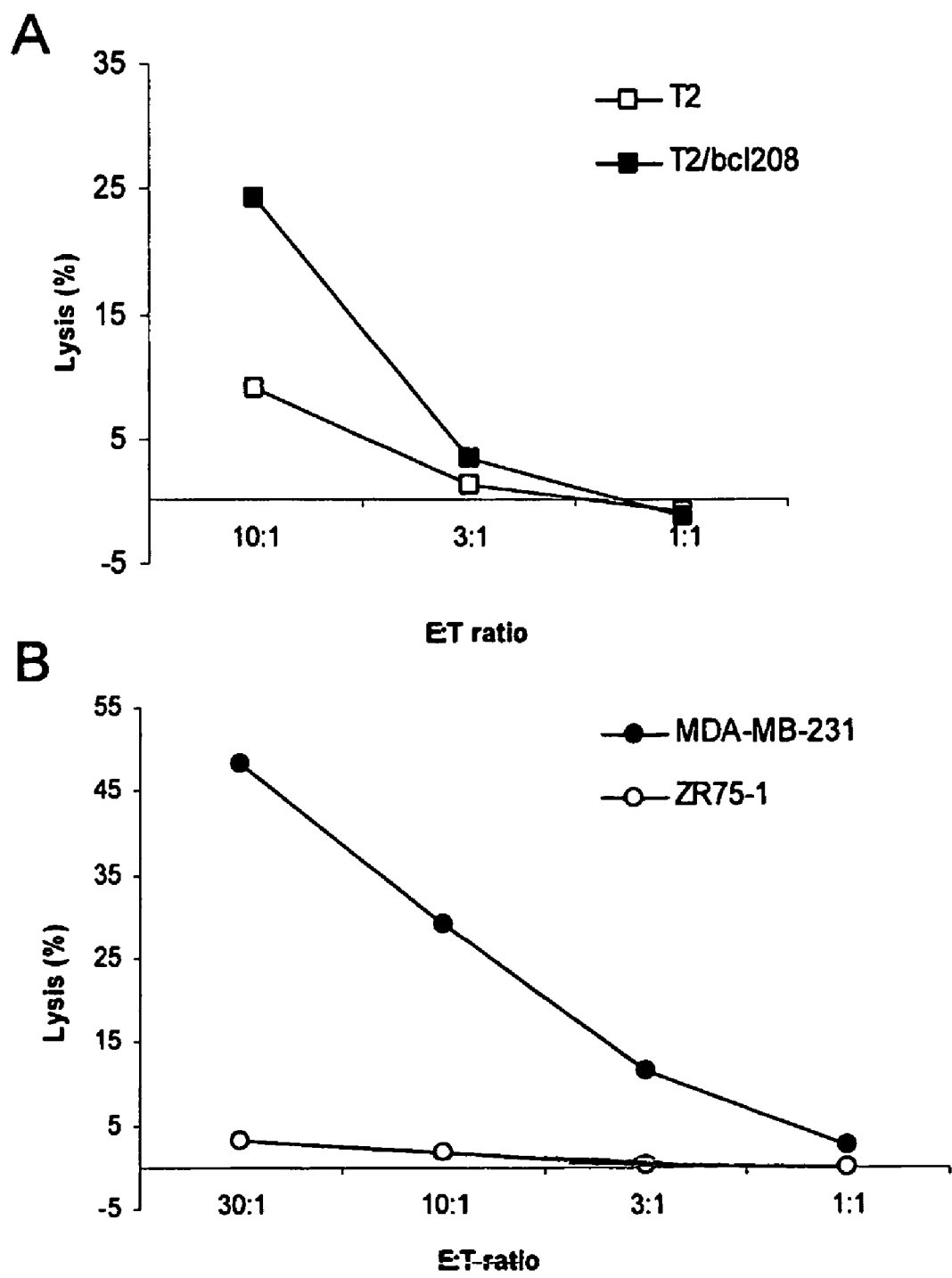

FIG. 5 illustrates the cytolytic capacity of Bcl-2 specific CTL. bcl$_{208}$ reactive CTL were isolated from PBL from a breast cancer patient using HLA-A2/bcl$_{208}$ coated magnetic beads. A) The isolated bulk culture were analyzed for specific lysis of T2 cells with (black square) or without (white square) bcl$_{208}$ peptide. B) Lysis by bcl$_{208}$-isolated T cells of the HLA-A2 positive breast cancer cell line MDA-MB-231 (black circle) and the HLA-A2 negative breast cancer cell line ZR75-1 (white circle).

Figure 6:
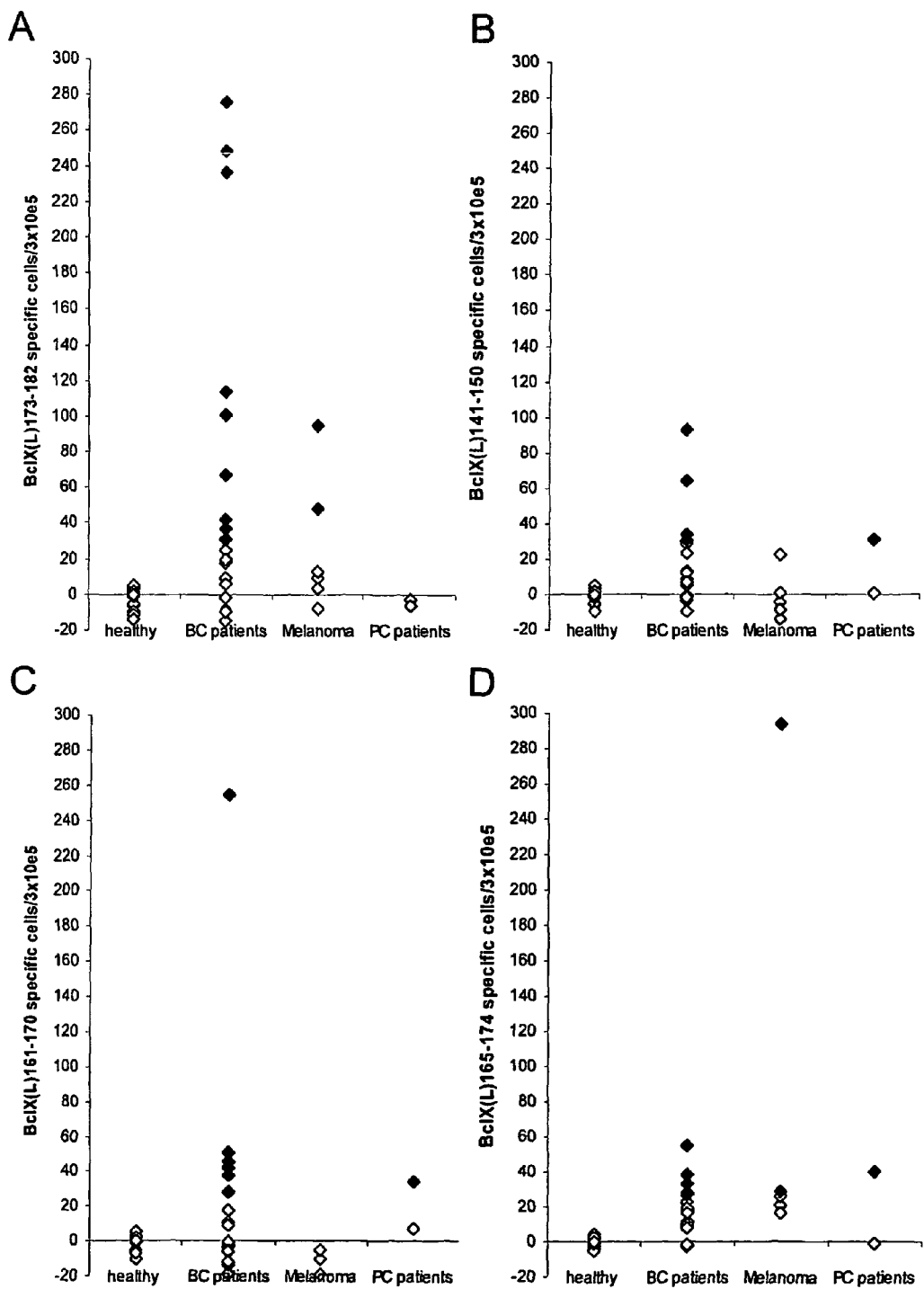

FIG. 6 illustrates HLA-A2 restricted T-cell responses against Bcl-X$_L$ as measured by INF-☐ ELISPOT. PBL from twelve healthy individuals, eighteen patients with breast cancer (BC patients), six melanoma patients and two pancreatic cancer patients (PC patients) were analyzed. All individuals were HLA-A2 positive. The peptides Bcl-X$_{L173-182}$ (YLNDHLEPWI)(SEQ ID NO:48) (A), Bcl-X$_{L141-150}$ (VAFFSFGGAL)(SEQ ID NO:49) (B), Bcl-X$_{L161-170}$ (VLVSRIAAWM)(SEQ ID NO:48) (C), and Bcl-X$_{L165-174}$ (RIAAWMATYL)(SEQ ID NO:45) (D) were examined. T-lymphocytes were stimulated once with peptide before being plated at $10^5$ cells per well in triplicates either without or with the relevant peptide. The average number of peptide specific spots (after subtraction of spots without added peptide) was calculated for each patient using the ImmunoSpot® Series 2.0 Analyzer (CTL Analyzers, LLC, Cleveland, US). Responders (defined as average number of antigen specific spots±½ standard deviation>25 per $10^5$ lymphocytes) are marked as black squares, whereas non-responding individuals are marked as white squares.

Figure 7:
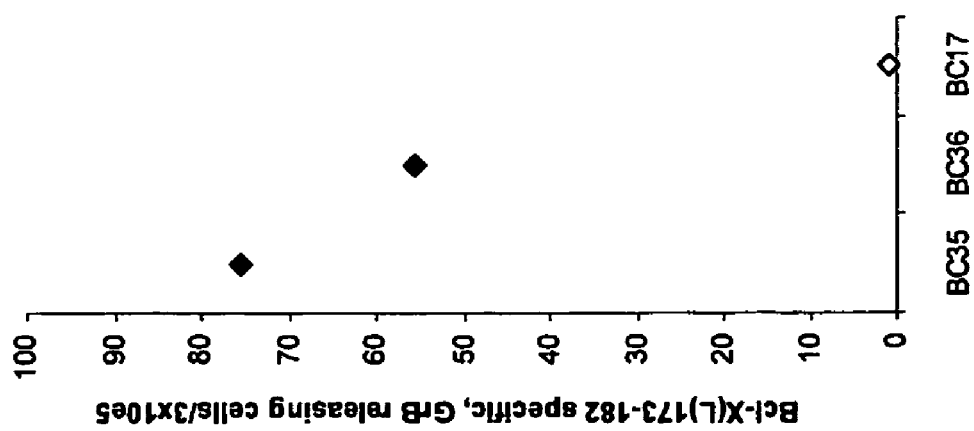

FIG. 7 illustrates detection of Bcl-X$_L$ specific CTL by granzyme B ELISPOT. T-lymphocytes from three different breast cancer patients (BC35, BC36, and BC17) were stimulated once with peptide before plated at $3 \times 10^5$ cells per well in triplicates either without or with peptide Bcl-X$_{L173-182}$ (YLNDHLEPWI). The average number of peptide specific Granzyme B spots (after subtraction of spots without added peptide) was calculated for each patient using the ImmunoSpot® Series 2.0 Analyzer (CTL Analyzers, LLC, Cleveland, US). Responders (defined as average number of antigen specific spots±½ standard deviation>25 per $10^5$ lymphocytes) are marked as black squares, whereas non-responding individuals are marked as white squares.

Figure 8:
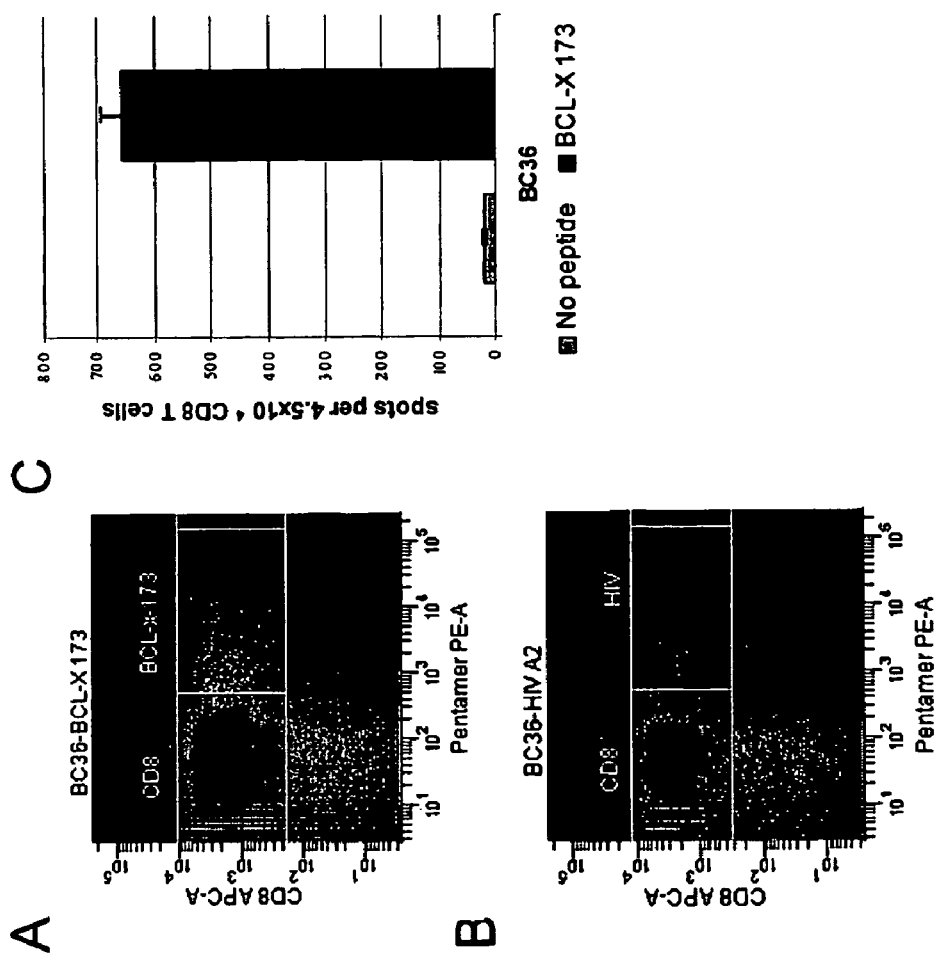

FIG. 8 illustrates analysis of Bcl-X$_L$ specific, CD8 positive cells in PBL from a breast cancer patient. PBL from patient BC36 were stimulated once with Bcl-X$_{L173-182}$ in vitro and the CD8+ cells were isolated before analysis. FACS staining of the culture using an anti-CD8 antibody and the pentamer complex HLA-A2/Bcl-X$_{L173-182}$ revealed that 95.5% of the cells were CD8 positive and 0.24% of these were pentamer positive (A). HLA-A2/HIV pentamer was used as a negative control (B). The cell culture was additionally analyzed by means of ELISPOT (C).

Figure 9:
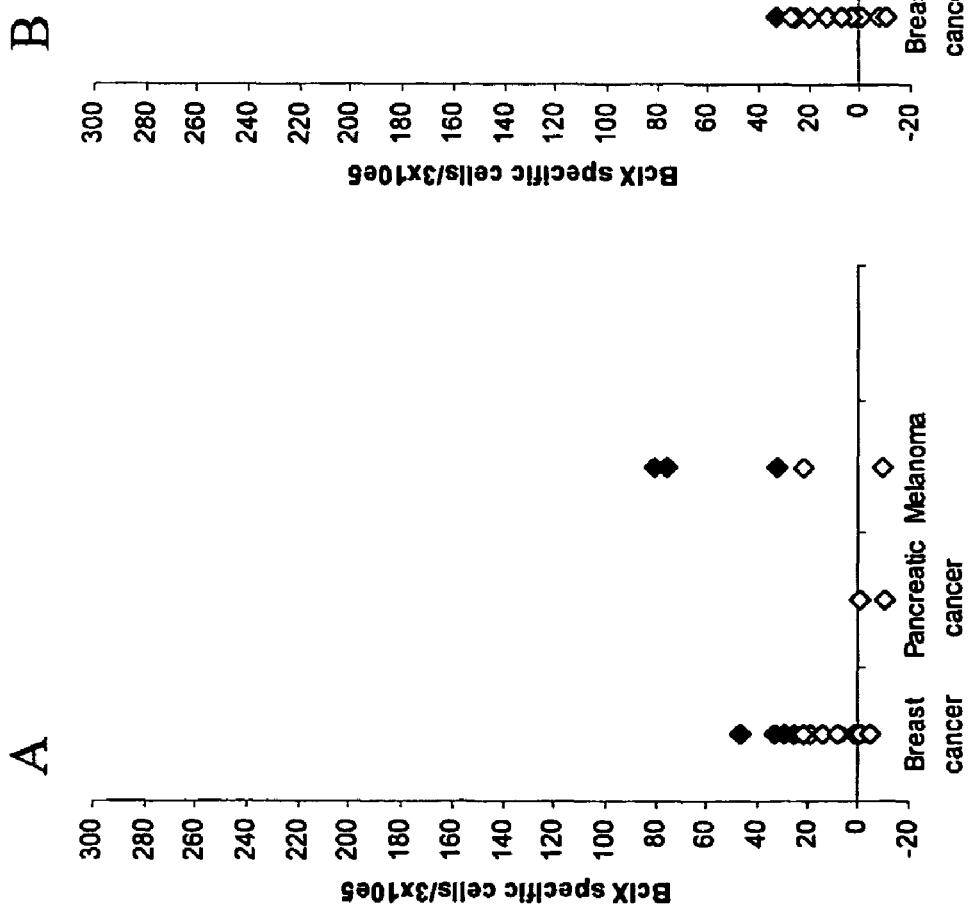

FIG. 9 illustrates HLA-A2 restricted T-cell responses against Bcl-X$_L$ as measured by INF-☐ ELISPOT. PBL from twelve healthy individuals, eighteen patients with breast cancer (BC patients), six melanoma patients and two pancreatic cancer patients (PC patients) were analyzed. All individuals were HLA-A2 positive. The peptides Bcl-X$_{L118-126}$ (TAYQSFEQV)(SEQ ID NO:43) (A) and Bcl-X$_{L169-178}$ (WMATYLNDHL)(SEQ ID NO:46) (B) were examined. T-lymphocytes were stimulated once with peptide before being plated at $10^5$ cells per well in triplicates either without or with the relevant peptide. The average number of peptide specific spots (after subtraction of spots without added peptide) was calculated for each patient using the ImmunoSpot® Series 2.0 Analyzer (CTL Analyzers, LLC, Cleveland, US). Responders (defined as average number of antigen specific spots±½ standard deviation>25 per $10^5$ lymphocytes) are marked as black squares, whereas non-responding individuals are marked as white squares.

Figure 10:
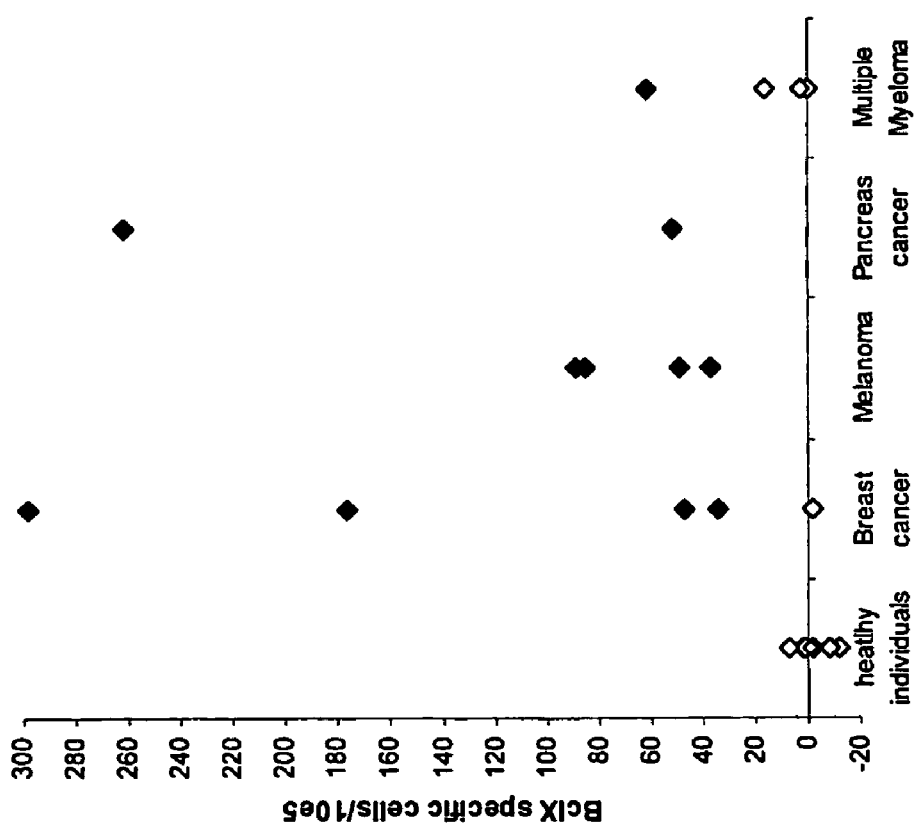

FIG. 10 illustrates HLA-A3 restricted T-cell responses against Bcl-X$_L$ as measured by INF-γ ELISPOT. T-lymphocytes were stimulated once with peptide before being plated at $10^5$ cells per well in triplicates either without or with the peptide Bcl-X$_{L165-173}$ (RIAAWMATY)(SEQ ID NO:50). PBL from seven healthy individuals, five patients with breast cancer, four melanoma patients, two pancreatic cancer patients, and five patients with multiple myeloma were examined. All individuals were HLA-A3 positive. The average number of peptide specific spots (after subtraction of spots without added peptide) was calculated for each patient using the ImmunoSpot® Series 2.0 Analyzer (CTL Analyzers, LLC, Cleveland, US).

Figure 11:
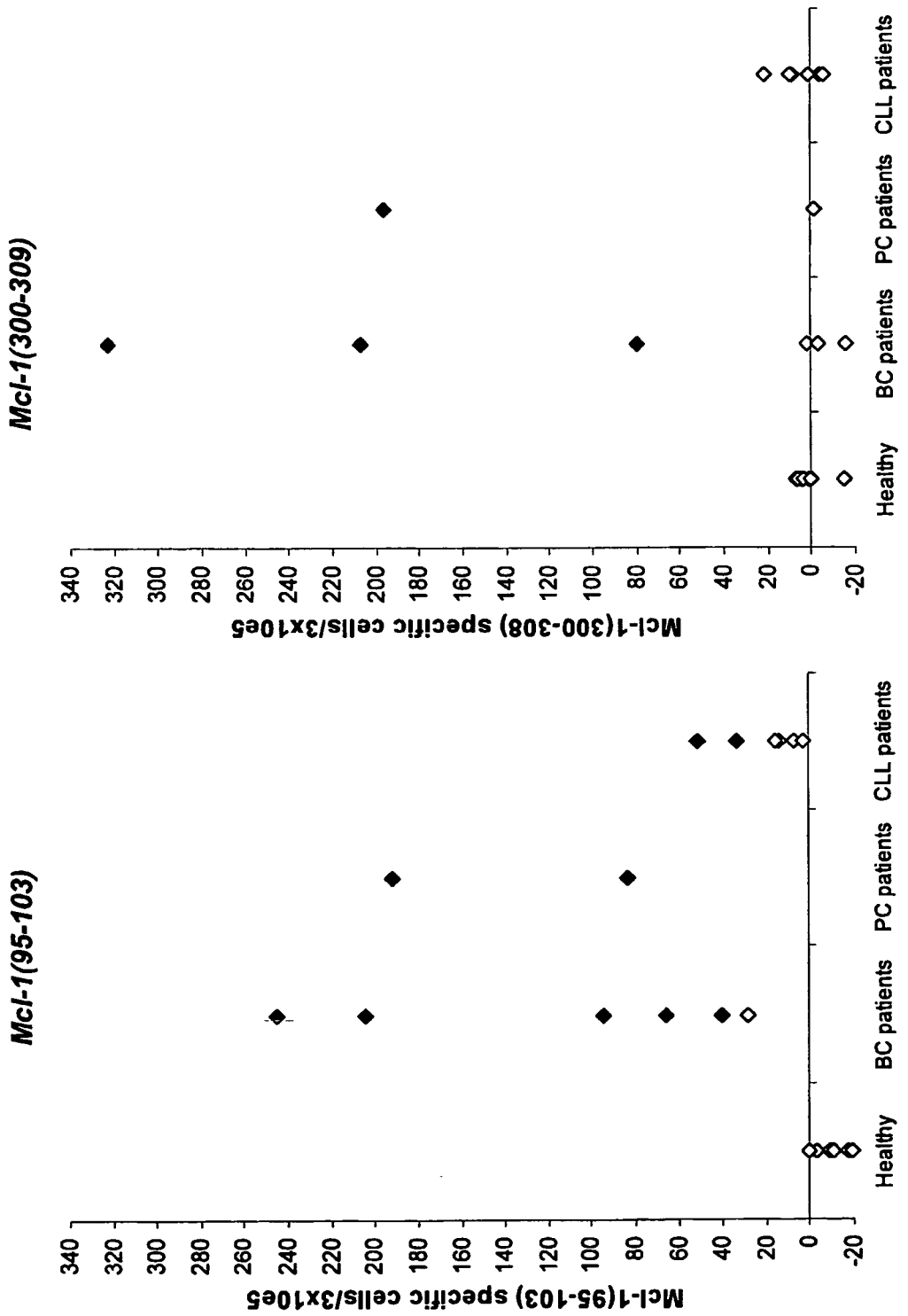

FIG. 11 illustrates HLA-A3 restricted T-cell responses against Mcl-1 as measured by INF-γ ELISPOT. T-lymphocytes were stimulated once with peptide before being plated at $3 \times 10^5$ cells per well in triplicates either without or with the peptide PBL from ten healthy individuals, six patients with breast cancer (BC), two pancreatic cancer (PC) patients, and six patients with CLL were examined against the Mcl-$1_{95-103}$ peptide (left) and the Mcl-$1_{300-308}$ peptide (right). All individuals were HLA-A3 positive. The average number of peptide specific spots (after subtraction of spots without added peptide) was calculated for each patient using the ImmunoSpot® Series 2.0 Analyzer (CTL Analyzers, LLC, Cleveland, US). Responders (defined as average number of antigen specific spots±½ standard deviation>25 per $10^5$ lymphocytes) are marked as black squares, whereas non-responding individuals are marked as white squares.

Figure 12:
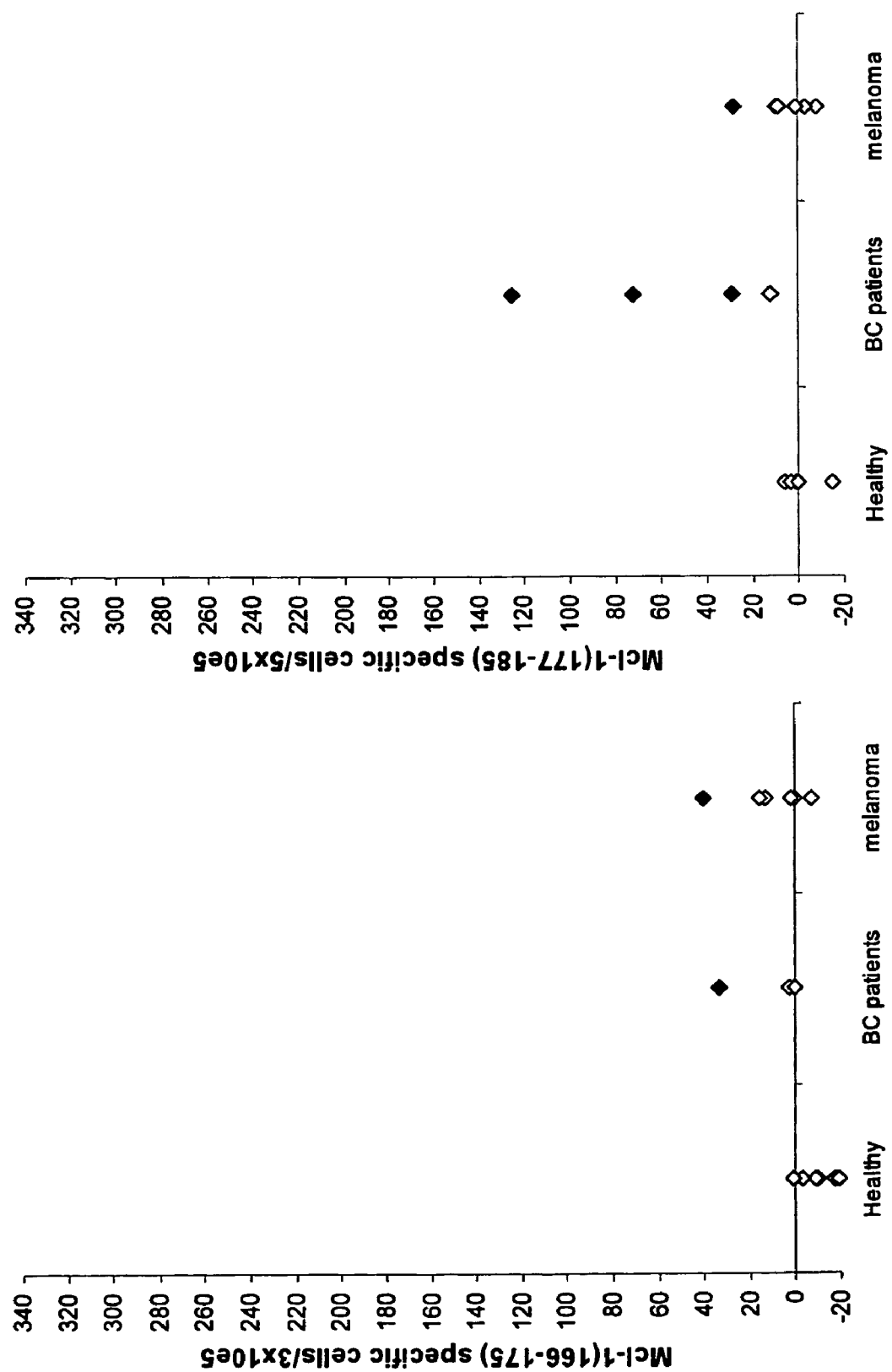

FIG. 12 illustrates HLA-A1 restricted T-cell responses against Mcl-1 as measured by INF-γ ELISPOT. T-lymphocytes were stimulated once with peptide before being plated at $3 \times 10^5$ cells per well in triplicates either without or with the peptide Mcl-$1_{166-175}$ or Mcl-$1_{177-185}$. PBL from six healthy individuals, four patients with breast cancer (BC), and seven melanoma patients were examined against the Mcl-$1_{95-103}$ peptide (left) and the Mcl-$1_{300-308}$ peptide (right). All individuals were HLA-A1 positive. The average number of peptide specific spots (after subtraction of spots without added peptide) was calculated for each patient using the ImmunoSpot® Series 2.0 Analyzer (CTL Analyzers, LLC, Cleveland, US). Responders (defined as average number of antigen specific spots±½ standard deviation >25 per $10^5$ lymphocytes) are marked as black squares, whereas non-responding individuals are marked as white squares.

EXAMPLES

Example 1

Immune responses against Bcl-2 in breast cancer patients

Materials and Methods

1. Patients

Peripheral blood lymphocytes (PBL) were collected from breast cancer patients. PBL were isolated using Lymphoprep separation, HLA-typed (Department of Clinical Immunology, University Hospital, Copenhagen, Denmark) and frozen in FCS with 10% DMSO. None of the patients received immunotherapy prior to sampling of blood.

2. Assembly Assay for Peptide Binding to MHC Class I Molecules

The binding affinity of the synthetic peptides (Invitrogen, Carlsbad, Calif., USA) to HLA-A2 molecules, metabolically labelled with [$^{35}$S]-methionine, was measured in the assembly assay, as described previously. The assay is based on peptide-mediated stabilisation of empty HLA molecules released upon cell lysis, from the TAP-deficient cell line T2. Stably folded HLA-molecules were immune-precipitated using the HLA class I-specific, conformation-dependent mAb W6/32, and separated by isoelectric focusing (IEF) gel electrophoresis. MHC heavy chain bands were quantified using the ImageGauge Phosphorimager program (FUJI photo film Co., Carrollton, Tex., USA). The intensity of the band is directly related to the amount of peptide-bound class I MHC complex recovered during the assay. Subsequently, the extent of stabilisation of HLA-A2 is directly related to the binding affinity of the added peptide. The recovery of HLA-A2 was measured in the presence of 50, 5, 0.5, 0.05 μM of the relevant peptide. The $C_{50}$ value was calculated for each peptide as the peptide concentration sufficient for half maximal stabilisation.

3. Antigen Stimulation of PBL

To extend the sensitivity of the ELISPOT assay, PBL were stimulated once in vitro prior to analysis. At day 0, PBL or crushed lymph nodes were thawed and plated in 2 ml/well at a concentration of $2 \times 10^6$ cells in 24-well plates (Nunc, Denmark) in X-vivo medium (Bio Whittaker, Walkersville, Md.), 5% heat-inactivated human serum, and 2 mM of L-glutamine in the presence of 10 μM of peptide. Two days later 20 IU/ml recombinant interleukin-2 (IL-2) (Chiron, Ratingen, Germany) was added to the cultures. The cultured cells were tested for reactivity in the ELISPOT on day 12.

4. ELISPOT Assay

The ELISPOT assay was used to quantify peptide epitope-specific interferon-γ releasing effector cells as described previously (4). Briefly, nitrocellulose bottomed 96-well plates (MultiScreen MAIP N45, Millipore, Hedehusene, Denmark) were coated with anti-IFN-γ antibody (1-D1K, Mabtech, Nacka, Sweden). The wells were washed, blocked by X-vivo medium, and cells added in duplicates at different cell concentrations. Peptides were then added to each well and the plates were incubated overnight. The following day, media was discarded and the wells were washed prior to addition of biotinylated secondary antibody (7-B6-1-Biotin, Mabtech). The plates were incubated for 2 hours, washed and Avidin-enzyme conjugate (AP-Avidin, Calbiochem, Life Technologies) was added to each well. Plates were incubated at RT for 1 hour and the enzyme substrate NBT/BCIP (Gibco, Life Technologies) was added to each well and incubated at RT for 5-10 min. The reaction was terminated by washing with tap-water upon the emergency of dark purple spots. The spots were counted using the ImmunoSpot® Series 2.0 Analyzer (CTL Analyzers, LLC, Cleveland, US) and the peptide specific CTL frequency could be calculated from the numbers of spot-forming cells. All assays were performed in triplicates for each peptide antigen.

5. Results

Binding of Bcl-2 Derived Peptides to HLA-A2

The amino acid sequence of the Bcl-2 protein was screened for the most probable HLA-A2 nona- and decamer peptide epitopes, using the main HLA-A2 specific anchor residues (2). Thirteen Bcl-2 derived peptides were synthesised and examined for binding to HLA-A2 by comparison with the HLA-A2 high affinity positive control epitope from HIV-1 pol$_{476-484}$ (ILKEPVHGV) (SEQ ID NO:39) by the assembly assay. The assembly assay is based on stabilisation of the class I molecule after loading of different concentrations of peptide to the TAP-deficient cell line T2. Subsequently correctly folded stable MHC heavy chains are immunoprecipitated using conformation-dependent antibodies. The extent of stabilisation of class I MHC molecules is directly related to the binding affinity of the added peptide as exemplified in FIG. 1. The peptide concentration required for half maximal recovery of class I MHC molecules ($C_{50}$ value) were 0.7 μM for the HIV-1 pol$_{476-484}$ (Table 1). Eight Bcl-2 derived peptides bound with almost similar high affinity as the positive control; Bcl$_{224}$, Bcl$_{85}$, Bcl$_{222}$, Bcl$_{218}$, Bcl$_{220}$, Bcl$_{214}$, Bcl$_{124}$ and Bcl$_{172}$ ($C_{50}$=0.7, 1, 1, 2, 1, 3, 1, and 2 μM, respectively) (Table 1). The peptides Bcl$_{80}$, Bcl$_{208}$ and Bcl$_{180}$ bound only with intermediate or weak affinity ($C_{50}$=36, 7 and 20 μM, respectively. Two of the peptides examined (Bcl$_{216}$, Bcl$_{200}$) did not bind to HLA-A2 at all. A list of the peptides included in this study are shown in Table 1:

TABLE 1

Peptides examined in this study

| Protein[a] | Sequence | SEQ ID NO | $C_{50}$ (μM)[b] |
|---|---|---|---|
| HIV-1 pol$_{476}$ | ILKEPVHGV | 39 | 0.7 |
| Bcl$_{224}$ | ALVGACITL | 1 | 0.7 |
| Bcl$_{85}$ | ALSPVPPVV | 2 | 1 |
| bcl$_{222}$ | SLALVGACI | 3 | 1 |
| bcl$_{218}$ | KTLLSLALV | 4 | 2 |
| bcl$_{220}$ | LLSLALVGA | 5 | 1 |
| bcl$_{214}$ | WLSLKTLLSL | 6 | 3 |
| bcl$_{80}$ | AAAGPALSPV | 7 | 36 |
| bcl$_{216}$ | SLKTLLSLAL | 40 | Not binding |
| bcl$_{208}$ | PLFDFSWLSL | 8 | 7 |
| bcl$_{124}$ | FTARGRFATV | 9 | 1 |
| bcl$_{180}$ | YLNRHLHTWI | 10 | 15 |
| bcl$_{172}$ | NIALWMTEYL | 11 | 2 |
| bcl$_{200}$ | ELYGPSMRPL | 41 | Not binding |

[a] The value range listed in subscript indicates the position of the first amino acid in the sequence
[b] The $C_{50}$ value is the concentration of the peptide required for half maximal binding to HLA-A2

CTL Responses Against BCL-2 Derived Peptides in Chemotherapy Treated Breast Cancer Patients Using the ELISPOT IFN-γ secretion assay, we examined the presence of specific T-cell responses against the Bcl-2 derived peptides in peripheral blood T cells from breast cancer patients. This method has previously been highly effective when identifying tumour specific CTL in cancer patients.

PBL from 15 HLA-A2 positive breast cancer patients were stimulated once in vitro before examination in the ELISPOT. This procedure was chosen to extend the sensitivity of the ELISPOT as described (4). Since many described CTL epitopes are in fact low affinity peptides we included all thirteen Bcl-2 deduced peptides in the first line of experiments. Responses were detected against Bcl$_{172}$, Bcl$_{180}$, Bcl$_{208}$, and Bcl$_{214}$ and only data from these peptides are given in FIG. 2. Spontaneous CTL responses were detected against Bcl$_{172}$ in PBL from eight of the patients (50%), and against Bcl$_{180}$ in four of the patients (≈25%) (FIG. 2). However, the most frequent responses were detected against Bcl$_{208}$ and Bcl$_{214}$, since twelve (≈80%) of the patients hosted a detectable CTL response against Bcl$_{208}$ and eleven of the patients (≈75%) hosted a Bcl$_{214}$-response (FIG. 2).

Example 2

Immunogenicity of Bcl-2 in Cancer Patients

Summary

Herein, we describe spontaneous T-cell reactivity against Bcl-2 in peripheral blood from patients suffering from unrelated tumor types, i.e., pancreatic cancer, AML and CLL. Additionally, we show that these Bcl-2 reactive T cells are indeed peptide specific, cytotoxic effector cells. Thus, Bcl-2 may serve as an important and widely applicable target for anti-cancer immunotherapeutic strategies, e.g., in the combination with conventional radiation- and chemotherapy.

Introduction

The Bcl-2 family comprises several key players in the regulation of apoptosis and includes both proapoptotic as well as antiapoptotic molecules. Bcl-2 is a critical cellular factor contributing to the pathogenesis and progression of cancer. In the present study, we examined the natural cellular immunogenicity of Bcl-2 in cancer patients.

Methods

Patients

PBL were isolated using Lymphoprep separation, HLA-typed (Department of Clinical Immunology, University Hospital, Copenhagen, Denmark) and frozen in FCS with 10% DMSO. None of the patients received immunotherapy prior to sampling of blood. Informed consent was obtained from the patients prior to any of theses measures. Peripheral blood lymphocytes (PBL) were collected from thirteen HLA-A2 positive breast cancer patients presenting with progressive disease with distant metastases defining stage IV disease; the majority of patients had more than one tumor location (8/13 patients). Prior treatment included chemotherapy, endocrine therapy, and radiation therapy. Eight patients were previously treated with chemotherapy, while five patients had only received endocrine therapy and no chemotherapy prior to study inclusion. Furthermore, twelve HLA-A2 positive patients with localized operable breast cancer were included and blood samples were collected prior to primary surgery and chemotherapy. Additionally, PBL were collected from two HLA-A2 positive pancreatic cancer patients presenting with progressive disease with distant metastases defining stage IV disease. Finally, PBL from ten HLA-A2 newly diagnosed CLL patients and three AML were collected prior to therapy. PBL from twelve HLA-A2 positive healthy individuals served as controls.

Granzyme B ELISPOT

The Granzyme B (GrB) ELISPOT assay was used for measuring antigen-specific CTL cytotoxicity as described. Briefly, nitrocellulose bottomed 96-well plates (MultiScreen MAIP N45, Millipore) were coated with GrB Capture Antibody (BD Biosciences, Brondby, Denmark). The wells were washed and blocked by X-vivo medium with 5% human serum. The cells were added at different cell concentrations. T2 cells and peptides were then added to each well and the plates were incubated 4 hours, medium was discarded and the wells were washed prior to addition of GrB Detection Antibody (BD Biosciences). The plates were incubated for 2 hours, washed and Avidin horseradish peroxidase (BD Biosciences) was added to each well. Plates were incubated at RT for 1 hour AEC Substrate Reagent (BD Biosciences) was added to each well and incubated at RT for 5-10 min. The reaction was terminated by washing with tap-water upon the emergency of red spots. The spots were counted and the peptide specific CTL frequency was calculated like for the INF-γ ELISPOT. All assays were performed in duplicate or triplicates for each peptide antigen.

Isolation of Peptide Specific T Cells

Antigen specific cells were isolated by means of Bcl$_{208}$/HLA-A2 coated magnetic beads as previously described. Biotinylated monomers (ProImmune, Oxford, UK) were coupled to streptavin coated magnetic beads (Dynabeads M-280, Dynal A/S, Oslo, Norway) by incubating 2.5 μg monomers with $5 \times 10^6$ beads in 40 μl PBS, for 20 min at room temperature. The magnetic complexes were washed three times in PBS in a magnetic field (Dynal A/S, Oslo, Norway) and subsequently mixed with PBLs, at a ratio of 1:10 in PBS with 5% BSA, and rotated very gently for 1 h. Antigen specific CD8$^+$ T cells associating with the magnetic complexes were gently washed three times. Isolated cells were resuspended numerous times in X-vivo with 5% HS, and incubated for 2 h, before the magnetic beads were released and removed from the cell suspension. The isolated cells were cultured in a 48-well plate in X-vivo, 5% HS and $10^6$ anti-CD28, anti-CD3 coated artificial cell-based antigen presenting cells (K32/41 BBL) that expresses 4-1BB ligand (4-1BBL) (kindly provided by Dr. Carl H. June, Department of Pathology and Laboratory Medicine, University of Pennsylvania). One day after isolation 20 units/ml IL-2 was added, and on day 5 the capacity of these cells to kill target cells was tested either in standard $^{51}$Cr release assays.

Cloning by Limiting Dilution

CTL clones were established from the isolated cultures by limiting dilution in 96-well plates using irradiated PBMC as feeder cells in the presence of 40 IU/ml IL-2 and 1 μg/ml HA in X-vivo with 5% HS. Fresh medium and IL-2 were added to the clones every 3-4 day.

Cytotoxicity Assay

Conventional [$^{51}$Cr]-release assays for CTL-mediated cytotoxicity was carried out as described elsewhere. Target cells were T2-cells with or without the relevant peptide, the HLA-A2-positive breast cancer cell line MDA-MB-231, and the HLA-A2-negative breast cancer cell line ZR75-1. Both breast cancer cell lines expressed Bcl-2 as examined by reverse transcription-PCR (data not shown).

Results

CTL Responses Against Bcl-2 Derived Peptides

To examine whether Bcl-2 specific T cells were also present in PBL from leukemia patients we examined PBL from ten HLA-A2 positive CLL patients and three AML patients for reactivity against the two peptides $bcl_{208}$ and $bcl_{214}$. Bcl-2 responses were present in five of the CLL patients and two of the AML patients (FIG. 3). Furthermore, we examined PBL from two pancreatic cancers and identified that both patients hosted a CTL response against the $bcl_{208}$ and $bcl_{214}$ peptides (FIG. 3). Similarly, PBL from 12 healthy HLA-A2 positive individuals were examined. Surprisingly, a weak CTL response was detected against the $bcl_{208}$ peptide in one of the healthy individuals (data not shown).

Bcl-2 Specific Granzyme B Release in PBL

Using the GrB ELISPOT we assessed whether the bcl-2 specific T cells detected in PBL exhibit cytotoxic function. Thus, PBL from three of the bcl-2 reactive breast cancer patients (pt. no.: 19, 20 and 22) were analyzed for reactivity against the two epitopes $bcl_{208}$ and $bcl_{214}$ (FIG. 4). In all three patients responses against both peptides could be detected with a frequency at about 50-140 peptide specific CTL per $10^5$ PBL. As a control we included a patient (pt. no.: 16), in which we could only detect a response against $bcl_{172}$ but not against $bcl_{208}$ and $bcl_{214}$ in the INF-γ ELISPOT and a healthy control (h1). As expected no GrB release was detected against $bcl_{208}$ or $bcl_{214}$ in neither the breast cancer patient no. 16 nor the healthy control.

The Functional Capacity of Bcl-2-reactive CTL

To further characterize the functional capacity of Bcl-2-reactive CTL, these cells were enriched by means of magnetic beads coated with HLA-A2/$bcl_{208}$-complexes as described. Cells were stimulated once with peptide in vitro prior to isolation. A small fraction of the isolated cells were cloned by limiting dilution. The expanding cultures were examined for recognition of T2 cells either without peptide or pulsed with $bcl_{208}$ in a GrB ELISPOT. Several of these clones showed specific recognition of $bcl_{208}$-pulsed T2 cells (data not shown). However, unfortunately we were not able to expand these clones for further analysis.

One day after isolation IL-2 was added to the remaining cells, and on day 5 the capacity of the cells to kill peptide loaded T2 cells was tested in standard $^{51}$Cr release assays. To this end, either unloaded T2 cells or T2 cells loaded with $bcl_{208}$ peptide served as targets. This assay revealed that only T2 cells pulsed with $bcl_{208}$ were killed (FIG. 5a). These enriched and in vitro stimulated $bcl_{208}$ reactive T cells were further used to test the capacity to kill the HLA-A2 positive, Bcl-2 expressing breast cancer cell line MDA-MB-231. The enriched T cells efficiently lysed the MDA-MB-231 cells, whereas in contrast, no cytotoxicity was observed against the Bcl-2 expressing, HLA-A2 negative breast cancer cell line ZR75-1 (FIG. 5b).

Example 3

Immunogenicity of Bcl-X(L) in cancer patients

Summary

Here, we demonstrate that Bcl-$X_L$ is a target for T-cell recognition in cancer patients. Thus, we describe spontaneous HLA-A2- and HLA-A3-restricted cytotoxic T-cell responses against peptide epitopes derived from Bcl-$X_L$ by means of ELISPOT and flow cytometry stainings. Thus, cellular immune responses against apoptosis inhibitors like the Bcl-2 family proteins appear to represent a general phenomenon in cancer, and consequently, this group of proteins represents attractive universal target proteins for anti-cancer immunotherapy. Additionally, since elevated expression of these proteins in cells is correlated with drug resistance, the combination of immunotherapy with cytotoxic chemotherapy is a very appealing way to treat cancer.

Introduction

The antiapoptotic protein Bcl-$X_L$ is produced from the long alternative splice form of the bcl-x gene, while proapoptotic Bcl-$X_S$ is derived from the short alternative splice form of the same gene. Bcl-$X_L$ plays an important role in cancer as it has been directly linked to resistance to conventional forms of therapies and poor prognosis. The functional inhibition of Bcl-$X_L$ restore the apoptotic process and render neoplastic cells sensitive to chemical and radiation therapies, whereas manipulation of cancer cell lines to express high levels of Bcl-$X_L$ results in a multi-drug reistance phenotype. Increased expression of Bcl-$X_L$ has been reported in a variety of different malignancies including AML and multiple myeloma as well as solid cancers like bladder cancer, breast cancer, pancreatic cancer and melanoma.

Ideal targets for immunotherapy are gene products silenced in normal tissues, overexpressed in cancer cells, and directly involved in tumor cell survival and progression.

Materials and Methods

Patients

Peripheral blood lymphocytes (PBL) were collected from patients suffering from cancer of different origin and from healthy controls and were isolated using Lymphoprep separation, HLA-typed (Department of Clinical Immunology, University Hospital, Copenhagen, Denmark) and frozen in FCS with 10% DMSO. None of the patients received immunotherapy prior to sampling of blood. Informed consent was obtained from the patients prior to any of theses measures.

Flow Cytometry (FACS)

PBL from a breast cancer patient was stimulated once in vitro with the relevant peptide and at day seven the CD8+ cells were isolated from PBL using the Dynal CD8 negative isolation kit (Dynal Biotech ASA, Oslo, Norway). The resulting CD8 positive T cell culture were stained with PE couplet Pro5™ MHC pentamers (ProImmune, Oxford, UK), followed by antibody staining with the flourochrome coupled mAbs: CD8-APC and CD3-FITC (Becton Dickinson, Immunocytometry Systems, San Jose, Calif.). Both stainings were performed in PBS+2% FCS, for 30 min, 4° C., in the dark. The Pro5™ MHC pentamer complexes used were: HLA-A2/Bcl-$X_{L173-182}$ (YLNDHLEPWI)(SEQ ID NO:42) and HLA-A2/HIV-1 $pol_{476-484}$ (ILKEPVHGV)(SEQ ID NO:39). The samples were analysed on BD FACS aria, using DIVA software (BD, San Jose, Calif.).

Results

Spontaneous CTL Responses Against Bcl-$X_L$ Derived Peptides

The bcl-x gene is transcribed into two mRNAs through alternative splicing. The antiapoptotic protein Bcl-$X_L$ is produced from the long alternative splice, while proapoptotic Bcl-$X_S$ is derived from the short alternative splice form of this gene. The protein product of the larger BCL-$X_L$ differs from Bcl-$X_S$ protein by an inserted region (amino acids 126-188). Thus, to investigate if Bcl-$X_L$ is a natural target for T-cells in cancer patients we scrutinized this inserted region (including nine amino acids at each end) for putative HLA-A2 epitopes using the main HLA-A2 specific anchor residues. Subsequently, we synthesized seven Bcl-$X_L$ deduced peptides (Bcl-$X_{L158-166}$ (EMQVLVSRI)(SEQ ID NO:44), Bcl-$X_{L118-126}$ (TAYQSFEQV)(SEQ ID NO:43), Bcl-$X_{L173-182}$ (YLNDHLEPWI)(SEQ ID NO:42), Bcl-$X_{L165-174}$ (RIAAWMATYL)(SEQ ID NO:45), Bcl-$X_{L169-178}$ (WMATYLNDHL)(SEQ ID NO:46), Bcl-$X_{L161-170}$ (VLVSRIAAWM)(SEQ ID NO:48), Bcl-$X_{L141-150}$ (VAFFSFGGAL)(SEQ ID NO:49)) and scrutinized PBL from HLA-A2+ cancer patients of different origin by means of ELISPOT against these peptides. This method has previously been shown to be highly effective to identify tumor specific CTL in cancer patients. Indeed, strong and frequent CTL responses were detected against four of the examined peptides (Bcl-$X_{L173-182}$, Bcl-$X_{L141-150}$, Bcl-$X_{L161-170}$, and Bcl-$X_{L165-174}$) in cancer patients of different origin (FIG. 6). Overall, fifteen out of eighteen HLA-A2+ breast cancer patients hosted an immune response against at least one of these four Bcl-$X_L$ peptides (responders are defined as average number of antigen specific cells±½ standard deviation >25 per $10^5$ cells). Likewise, four out of six examined melanoma patients and one out of two examined pancreatic cancer patients hosted an immune response against at least one of these four peptides. Thus, nine out of eighteen examined breast cancer patients hosted an immune response against Bcl-$X_{L173-182}$, whereas two out of six examined HLA-A2+ melanoma patients hosted an immune response against this peptide (FIG. 6a). Four out of eighteen examined breast cancer patients hosted an immune response against Bcl-$X_{L141-150}$, whereas we detected responses in PBL from one of the two pancreatic cancer patients examined. We were not able to detect a response in PBL from any of the five melanoma patients examined against this peptide (FIG. 6b). Likewise, we detected a response in PBL from six breast cancer patients, and one examined pancreatic cancer patient against Bcl-$X_{L161-170}$ (FIG. 6c). Finally, four breast cancer patients, two melanoma patients and one pancreatic cancer patient hosted a response against Bcl-$X_{L165-174}$ (FIG. 6d). As control PBL from 12 healthy HLA-A2+ individuals were examined. Importantly, no responses were detected against either Bcl-$X_{L173-182}$, Bcl-$X_{L141-150}$, Bcl-$X_{L161-170}$, or Bcl-$X_{L165-174}$ peptide in any of the healthy individuals (FIG. 6)

Bcl-$X_L$ Specific Granzyme B Release in PBL

Using the GrB ELISPOT we assessed whether the Bcl-$X_L$ specific T cells detected in PBL exhibit cytotoxic function. Thus, PBL from two of the Bcl-$X_L$ reactive breast cancer patients (pt. no.: 35 and 36) were analyzed for reactivity against Bcl-$X_{L173-182}$ (FIG. 7). In both patients responses against Bcl-$X_{L173-182}$ could be detected with a frequency at about 50-100 peptide specific CTL per $3 \times 10^5$ cells. As a control we included a patient (pt. no.: 17), in which we could only detect a response against Bcl-$X_{L141-150}$ but not against Bcl-$X_{L173-182}$ in the INF-γ ELISPOT. As expected, no GrB release was detected against Bcl-$X_{L173-182}$ in breast cancer patient no. 17.

FACS Analyses of Bcl-$X_L$ Specific T Cells

The spontaneous occurrence of Bcl-$X_{L173-182}$ specific CTL in PBL from breast cancer patients was further evaluated using FACS analyses and Pro5™ MHC Pentamer staining. PBL from breast cancer patient no. 36 were stimulated once in vitro with peptide and the CD8 positive cells were isolated. This culture was stained with the HLA-A2/BCL-X pentamer complex. FACS analyses revealed an easily detectable population of pentamer positive T cells constituting 0.24% of the CD8+ T cells (FIG. 8a). In comparison, the same CD8+ T-cells showed around 1.4% Bcl-$X_{L173-182}$ specific, IFNγ secreting CD8+ T cells when analysed by means of ELISPOT (FIG. 8c).

Additional HLA-A2 Restricted Epitopes Against Bcl-X(L)

We scrutinized PBL from HLA-A2+ cancer patients of different origin by means of ELISPOT against Bcl-$X_{L118-126}$ (TAYQSFEQV)(SEQ ID NO:43) (FIG. 9a) and Bcl-$X_{L169-178}$ (WMATYLNDHL)(SEQ ID NO:46) (FIG. 9b) identifying a weak spontaneous CTL response in cancer patients of different origin against both peptides.

HLA-A3-restricted Responses Against Bcl-X(L)

Additionally, we scrutinized the inserted region (including nine amino acids at each end) for putative HLA-A3 epitopes using the main HLA-A3 specific anchor residues. Subsequently, we synthesized two peptides; Bcl-$X_{L165-173}$ (RIAAWMATY)(SEQ ID NO:50) and the Bcl-$X_{L149-157}$ (ALCVESVDK)(SEQ ID NO 51). Next, we scrutinized PBL from HLA-A3+ cancer patients of different origin by means of ELISPOT against the Bcl-$X_{L165-173}$ (RIAAWMATY) (SEQ ID NO: 50) and the Bcl-$X_{L149-157}$ (ALCVESVDK) (SEQ ID NO:51) peptide. This method has previously been shown to be highly effective to identify tumor specific CTL in cancer patients. Indeed, strong and frequent CTL responses were detected against Bcl-$X_{L165-173}$ (RIAAWMATY)(SEQ ID NO:50) in cancer patients of different origin, We were able to detect a response against the Bcl-$X_{L165-173}$ in HLA-A3+ PBL in four out of five examined breast cancer patients (responders are defined as average number of antigen specific cells±½ standard deviation >25 per $10^5$ cells), four out of four examined melanoma patients, two out of two examined pancreatic cancer patients as well as one out of four examined multiple myeloma patients (FIG. 10). Importantly, we were not able to detect a response in any of the seven HLA-A3+ healthy individuals we examined as controls (FIG. 10).

Example 4

Immunogenicity of Mcl-1 in Cancer Patients

Summary

Here, we demonstrate that Mcl-1 is a target for T-cell recognition in cancer patients. Thus, we describe spontaneous HLA-A1- and HLA-A3-restricted cytotoxic T-cell responses against peptide epitopes derived from Mcl-1 by means of ELISPOT Introduction Myeloid cell factor-1 (Mcl-1) is a death-inhibiting member of the Bcl-2 family that is expressed in early monocyte differentiation and can promote viability on transfection into immature myeloid cells. Mcl-1 in transgenic mice promotes survival in a spectrum of hematopoietic cell types and immortalization of myeloid cells. Elevated levels of Mcl-1 have been reported for a number of human cancers including prostate cancers, pancreatic cancers, melanoma, breast cancers, ovarian cancer patients, and cervical cancer, as well as B-cell chronic lymphocytic leukemia (B-CLL) and in AML and ALL upon relapse. In B-CLL patients, higher levels of Mcl-1 are strongly correlated with failure to achieve complete remission after single-agent therapy. In multiple myeloma, Mcl-1 plays an important role in the survival of malignant cells. In this regard it has been demonstrated that mice expressing a mcl-1 transgene under control of its own promoter develop B-cell neoplasias with high frequency, ranging from follicular lymphoma to diffuse large cell lymphoma.

HLA-A3-restricted Responses Against Mcl-1

To investigate whether Mcl-1 is a natural target for T-cells in cancer patients we examined the protein sequence for the most probable HLA-A3 nona- and deca-mer peptide epitopes, using the main HLA-A3 specific anchor residues. Subsequently, we synthesized six Mcl-1 deduced peptides (Mcl-1$_{185-194}$ (YLREQATGAK)(SEQ ID NO:52), Mcl-1$_{293-302}$ (SITDVLVRTK)(SEQ ID NO:53), Mcl-1$_{267-276}$ (LISFGAFVAK)(SEQ ID NO:54), Mcl-1$_{95-103}$ (RLLFFAPTR)(SEQ ID NO:55), Mcl-1$_{300-308}$ (RTKRDWLVK)(SEQ ID NO:56), Mcl-1$_{236-244}$ (DIKNEDDVK)(SEQ ID NO:57)) and scrutinized PBL from HLA-A3+ cancer patients of different origin for reactivity against these peptides, taking advantage of the ELISPOT assay. This method has previously been shown to be highly efficient for identification of tumor specific CTL in cancer patients. Indeed, strong and frequent CTL responses were detected against two Mcl-1 derived peptides in cancer patients of different origin (Mcl-1$_{95-103}$ and Mcl-1$_{300-308}$) (FIG. 11). Overall, five out of six examined HLA-A3+ breast cancer patients hosted an immune response against one of these two Mcl-1 peptides. Thus, five breast cancer patients hosted a response against Mcl-1$_{95-103}$ (responders are defined as average number of antigen specific cells±½ standard deviation >25 per 10$^5$ cells), and three patients hosted a response against Mcl-1$_{300-308}$ (FIG. 11). Additionally, two out of two examined HLA-A3+ pancreatic cancer patients hosted an immune response against the Mcl-1$_{95-103}$ peptide, whereas one of these also reacted against Mcl-1$_{300-308}$. Additionally, we examined the PBL from six patients suffering from B-CLL and identified a response against Mcl-1$_{95-103}$ in two of these patients. As a control PBL from 10 healthy HLA-A3+ individuals were examined. Importantly, no responses were detected against either the Mcl-1$_{95-103}$ or the Mcl-1$_{300-308}$ peptide in any of the healthy donors (FIG. 11). Similarly, no responses could be detected against any of the additional four Mcl-1 derived peptides in any of the cancer patients or healthy controls (data not shown).

HLA-A1-restricted Responses Against Mcl-1

To investigate whether Mcl-1 is a natural target for T-cells in cancer patients we examined the protein sequence for the most probable HLA-A1 nona- and deca-mer peptide epitopes, using the main HLA-A1 specific anchor residues. Subsequently, we synthesized four Mcl-1 deduced peptides (Mcl-1$_{166-175}$ (PAEEEEDDLY)(SEQ ID NO:58), Mcl-1$_{121-129}$ (SPEEELDGY)(SEQ ID NO:59), Mcl-1$_{177-185}$ (QSLEIISRY)(SEQ ID NO:60), Mcl-1$_{339-347}$ (AGVGAGLAY)(SEQ ID NO:61)) and scrutinized PBL from HLA-A1+ cancer patients of different origin for reactivity against these peptides, taking advantage of the ELISPOT assay. Indeed, CTL responses were detected against two Mcl-1 derived peptides in cancer patients of different origin (Mcl-1$_{166-175}$ and Mcl-1$_{177-185}$) (FIG. 12). Overall, three out of four examined HLA-A1+ breast cancer patients hosted an immune response against Mcl-1$_{177-185}$ and one of these in addition hosted a response against Mcl-1$_{166-175}$ (FIG. 12). Additionally, one out of seven melanoma patients hosted an immune response against the Mcl-1$_{177-185}$ peptide, and another of these hosted a response against Mcl-1$_{166-175}$. As a control PBL from six healthy HLA-A1+ individuals were examined. Importantly, no responses were detected against either the Mcl-1$_{166-175}$ or the Mcl-1$_{177-185}$ peptide in any of the healthy donors (FIG. 12).

Modified Peptide Responses

The immunogenicity of the HLA-A3 restricted peptide Mcl-1$_{300-308}$ was increased by replacing threonine at position 2 with a better HLA-A3 anchor residue namely Leucine (Mcl-1$_{300-308}$L2 (RLKRDWLVK)(SEQ ID NO:62)). Spontanous immune responses were detected in two Breast cancer patients against Mcl-1$_{300-308}$L2 (data not shown). Likewise, to generate more immunogenetic epitope we modified the HLA-A1 restricted peptide Mcl-1$_{177-185}$ (QSLEIISRY)(SEQ ID NO:60) at position 3 generating the two peptides Mcl-1$_{177-185}$D3 (QSDEIISRY)(SEQ ID NO:63) and Mcl-1$_{177-185}$E3 (QSEEIISRY)(SEQ ID NO:64).

Discussion

Almost all malignancies are characterized by defects in apoptosis signaling. This renders the malignant cells resistant to endogenous apoptotic stimuli, as well as exogenous stimuli such as chemotherapeutic drugs and radiation. The defective apoptosis seen in human cancers are often results from overexpression of antiapoptotic proteins in the Bcl-2 protein family, i.e., Bcl-2, Bcl-X$_L$, and Mcl-1, Bcl-w, Bfl-1A1, Bcl-b, and Bcl2-L-10 Using such inhibitors of apoptosis proteins for vaccination purposes is advantegous because downregulation or loss of expression of these proteins as some form of immune escape would impair sustained tumor growth, since survival of tumor cells requires functionally active members of the Bcl-2 family. For therapeutic strategies, targeting of antigens that plays an insignificant role in relation to tumor cell growth and survival, the selection of antigen deficient tumors is a well-recognized limitation. In addition, since elevated expression of Bcl-2 family proteins in cells is correlated with drug resistance, the combination of a Bcl-2 family-based immunotherapy with cytotoxic chemotherapy is a very exciting new way to treat cancer.

We scanned the Bcl-2, Bcl-X(L) and Mcl-1 proteins for the presence of peptide binding motifs and used these to search for specific T-cell responses in cancer patients. To this end, spontaneous T-cell reactivity was detected against all members of the Bcl-2 family in patients suffering from unrelated tumor types, i.e., pancreatic cancer, breast cancer, melanoma AML and CLL by means of ELISPOT. The presence of Bcl-$X_L$ specific CD8+ cells in PBL from cancer patients was confirmed by CD8/pentamer FACS stainings. Taken together, these data shows that CTL defined epitopes from these proteins might be broadly applicable in therapeutic vaccinations against cancer and are therefore of substantial immunotherapeutic value.

In addition, eleven of the breast cancer patients possessed Bcl-2 specific CTLs, eight of these patients were previously treated with at least one type of chemotherapy. In two patients (pt. no: 14 and 17) no CTL responses to the four different Bcl-2 peptides were detectable. Both patients had previously received anti-hormonal therapy but no chemotherapy. Similarly, we were not able to detect any responses in patients with primary localized breast cancer prior to chemotherapy. Thus, in breast cancer patients Bcl-2 responses were only detected in the patients who had received chemotherapy. Although, tumor load may play an important role, this might indicate that the immune responses are introduced or increased as a consequence of the treatment-induced increase of Bcl-2 expression. It points to a scenario in which the combination of a Bcl-2-family based immunotherapy with cytotoxic chemotherapy might in a synergy improve current response rates. The treatment status of the patients examined for Bcl-X(L) and Mcl-1 responses was not available.

In the present study we took advantage of the GrB ELISPOT assay to demonstrate that the Bcl-2 or Bcl-X(L) specific CTL in the patients PBL are indeed cytotoxic effector cells. To further prove this notion, we enriched Bcl-2 reactive T cells from patient PBL, and showed that the resulting T-cell line was able to lyse peptide-pulsed T2-cells in a conventional 51Cr-release assay. Moreover, this Bcl-2 reactive T-cell line was capable of killing a HLA-matched breast cancer cell line, whereas HLA-A2 negative target cells was not killed. These findings shows that cancer cells indeed process and present the Bcl-2 peptide in the context of the HLA-A2 molecule. Finally, we were able to clone these isolated cells and showed that they reacted highly specific against the Bcl-2 peptide epitope.

When peptides derived from melanocyte differentiation antigens were first used to treat patients with stage IV melanoma it was envisioned that this might lead to pronounced destruction of melanocytes, which in turn would manifest clinically, i.e., vitiligo or retinitis. However, clinical experience demonstrated that the incidence of vitiligo in patients receiving vaccinations was not significantly higher than the incidence of melanoma associated hypopigmentation in patients receiving other forms of therapy. Additionally, no serious site-effects have been reported in various vaccination trails against self-antigens. Our data taken together prove that cellular immune responses against the group of Bcl-2 family proteins are a general feature in cancer. In attempt to maximize the impact of immunotherapy, an exciting strategy would be to consider the expression profile and prognostic significance of the chosen target in the particular disease, or disease stage, being treated. Thus, while coexpression of Bcl-2, Mcl-1 and Bcl-$X_L$ is seen in some cancers, or a particular stage of disease, other cancers exhibit exclusive expression of one or the other protein. Thus, in some diseases like ovarian cancer, expression of Mcl-1, but not Bcl-2, is associated with advanced stage and poor survival for which reason Mcl-1 might be the prime antigen, whereas in diseases such as CLL, where Bcl-2 and Mcl-1 are co-over expressed, simultaneous targeting of both proteins may represent a more effective strategy than targeting either molecule alone. Similary, Tanaka et al described that the presence of another inhibitor-of-apoptosis protein survivin in breast carcinoma was strongly associated with expression of Bcl-2 and with reduced apoptotic index (AI) and poor overall survival. A similar association between survivin and Bcl-2 has been described in neuroblastoma, gastric cancer, colorectal cancer, and high-grade non-Hodgkin's lymphoma. The safety and potential efficacy of survivin derived peptides in therapeutic vaccinations against cancer is currently being investigated in phase I/II clinical trials (J. Becker, personal communication). Thus, an exciting immunotherapeutic strategy would be to target both Bcl-2 protein family and survivin especially since they execute their anti-apoptotic function though different cellular pathways.

Example 5

Peptide Vaccine

Bcl-2 protein family peptides can e.g. be synthesized e.g. at the UVA Biomolecular Core Facility with a free amide $NH_2$ terminus and free acid COOH terminus. Each is provided as a lyophilized peptide, which is then reconstituted in sterile water and diluted with Lactated Ringer's solution (LR, Baxter Healthcare, Deerfield, Ill.) as a buffer for a final concentration of 67-80% Lactated Ringer's in water. These solutions are then sterile-filtered, placed in borosilicate glass vials, and submitted to a series of quality assurance studies including confirmation of identity, sterility, general safety, and purity, in accordance with FDA guidelines, as defined in IND 6453. Tests of peptide stability demonstrated no decrease in purity or in the peptide concentration, when these peptide solutions were stored at −20° C. for 3 years.

In practical circumstances, patients will receive a vaccine comprising about 100 μg of a class I HLA-restricted peptide with or without a class II HLA-restricted helper peptide. The patients are vaccinated with e.g. about 100 μg of the class I HLA peptide in adjuvant alone, or are vaccinated with e.g. about 100 μg of the HLA class I-restricted peptide plus 190 μg of the class II-restricted helper peptide. The higher dose of the helper peptide is calculated to provide equimolar quantities of the helper and cytotoxic epitopes. Additionally, patients can be vaccinated with a longer peptide comprising the amino acid sequences of both peptides.

The above peptides, in 1-ml aqueous solution, can be administered either as a solution/suspension with about 100 μg of QS-21, or as an emulsion with about 1 ml of Montanide ISA-51 adjuvant.

Patients are immunized e.g. at day 0 and months 1, 2, 3, 6, 9, and 12, with the peptides plus adjuvant, for a total of seven immunizations. With rare exceptions, the vaccinations are administered to the same arm with each vaccine. The peptides are preferably administered s.c.

REFERENCES

1. Altieri, D. C., Marchisio, P. C., and Marchisio, C. Survivin apoptosis: an interloper between cell death and cell proliferation in cancer. Lab Invest, 79: 1327-1333, 1999.
2. Andersen, M. H., L. Tan, I. Sondergaard, J. Zeuthen, T. Elliott, and J. S. Haurum. 2000. Poor correspondence between predicted and experimental binding of peptides to class I MHC molecules. *Tissue Antigens* 55:519.
3. Reed, J. C. 1998. Bcl-2 family proteins. *Oncogene* 17:3225.
4. Andersen, M. H., L. O. Pedersen, J. C. Becker, and P. thor Straten. 2001. Identification of a Cytotoxic T Lymphocyte Response to the Apoptose Inhibitor Protein Survivin in Cancer Patients. *Cancer Res.* 61:869.
5. Thurner, B., Roder, C., Dieckmann, D., Heuer, M., Kruse, M., Glaser, A., Keikavoussi, P., Kampgen, E., Bender, A., and Schuler, G. (1999) Generation of large numbers of fully mature and stable dendritic cells from leukapheresis products for clinical application J. Immunol. Methods 223, 1.
6. Shangary S and Johnson D E (2003) Recent advances in the development of anticancer agents targeting cell death inhibitors in the Bcl-2 protein family. *Leukemia* 17:1470-1482
7. Rosenberg S A and Dudley M E (2004) Cancer regression in patients with metastatic melanoma after the transfer of autologous antitumor lymphocytes. *PNAS* 101:14639-14645

The invention claimed is:

1. A vaccine composition comprising an immunogenically active peptide wherein the peptide consists of at the most 15 amino acids and comprises SEQ ID NO:8 or a sequence which differs from SEQ ID NO:8 by one or two amino acid substitutions.

2. The composition of claim 1, wherein the vaccine composition when administered to a cancer patient, is capable of eliciting an immune response against the cancer disease.

3. The composition of claim 1, wherein the vaccine composition, when administered to a cancer patient where a Bcl-2 protein family member is expressed, is capable of eliciting an immune response against the cancer disease.

4. The vaccine composition of claim 1, wherein the peptide is a fragment of Bcl-2.

5. An isolated immunogenically active peptide, wherein the peptide consists of at the most 15 amino acids and comprises SEQ ID NO:8 or a homologue thereof differing from SEQ ID NO:8 by one or two amino acid substitutions.

6. The peptide according to claim 5, wherein the peptide is a fragment of Bcl-2.

7. The peptide according to claim 5 that is capable of eliciting a cellular immune response in a cancer patient.

8. The peptide according to claim 5, which is an MHC Class I-restricted peptide having at least one of the following characteristics:

(i) capable of binding to the Class I HLA molecule to which it is restricted at an affinity as measured by the amount of the peptide that is capable of half maximal recovery of the Class I HLA molecule ($C_{50}$ value) which is at the most 50 µl as determined by the assembly binding assay as described herein, (ii) capable of eliciting INF-γ-producing cells in a PBL population of a cancer patient at a frequency of at least 1 per $10^4$ PBLs as determined by an ELISPOT assay, and/or (iii) capable of in situ detection in a tumor tissue of CTLs that are reactive with the epitope peptide.

9. The peptide of claim 8 having a $C_{50}$ value, which is at the most 30 μM.

10. The peptide of claim 8 having a $C_{50}$ value, which is at the most 20 μM.

11. The peptide of claim 8, which is restricted by a MHC Class I HLA-A molecule.

12. The peptide of claim 11, which is restricted by a MHC Class I HLA species selected from the group consisting of HLA-A1, HLA-A2, HLA-A3, HLA-A11 and HLA-A24.

13. The peptide of claim 8, which is restricted by HLA-A2.

14. The peptide according to claim 5, which comprises PLFDFSWLSL (SEQ ID NO:8).

15. The peptide of claim 8, which is restricted by a MHC Class I HLA-B molecule.

16. The peptide of claim 15, which is restricted by a MHC Class I HLA-3 species selected from the group consisting of HLA-B7, HLA-B35, HLA-B44, HLA-B8, HLA-B15, HLA-B27 and HLA-B51.

17. The peptide of claim 5, which is a decapeptide.

18. The peptide according to claim 5 comprising, for each specific HLA allele, any of the amino acid residues as indicated in the following table:

| HLA allele | Position 1 | Position 2 | Position 3 | Position 5 | Position 6 | Position 7 | C-terminal |
|---|---|---|---|---|---|---|---|
| HLA-A1 | | T, S | D, E | | | L | Y |
| HLA-A2 | | L, M | | | V | | L, V |
| HLA-A3 | | L, V, M | F, Y | | | | K, Y, F |
| HLA-A11 | | V, I, F, Y | M, L, F, Y, I | | | | K, R |
| HLA-A23 | | I, Y | | | | | W, I |
| HLA-A24 | | Y | | I, V | F | | I, L, F |
| HLA-A25 | | M, A, T | I | | | | W |
| HLA-A26 | E, D | V, T, I, L, F | | | I, L, V | | Y, F |
| HLA-A28 | E, D | V, A, L | | | | | A, R |
| HLA-A29 | | E | | | | | Y, L |
| HLA-A30 | | Y, L, F, V | | | | | Y |
| HLA-A31 | | | L, M, F, Y | | | | R |
| HLA-A32 | | I, L | | | | | W |
| HLA-A33 | | Y, I, L, V | | | | | R |
| HLA-A34 | | V, L | | | | | R |
| HLA-A66 | E, D | T, V | | | | | R, K |
| HLA-A68 | E, D | T, V | | | | | R, K |
| HLA-A69 | | V, T, A | | | | | V, L |
| HLA-A74 | | T | | | | | V, L |
| HLA-B5 | | A, P | F, Y | | | | I, L |
| HLA-B7 | R, A | P | | | | | L, F |
| HLA-B8 | | | K | K, R | | | L |
| HLA-B14 | | R, K | | | | | L, V |
| HLA-B15 (B62) | | Q, L, K, P, H, V, I, M, S, T | | | | | F, Y, W |
| HLA-B17 | | | | | | | L, V |
| HLA-B27 | | R | | | | | Y, K, F, L |
| HLA-B35 | | P | | | | | I, L, M, Y |
| HLA-B37 | | D, E | | | | | I, L, M |
| HLA-B38 | | H | D, E | | | | F, L |
| HLA-B39 | | R, H | | | | | L, F |
| HLA- | | E | F, I, V | | | | L, V, A, W, |

-continued

| HLA allele | Position 1 | Position 2 | Position 3 | Position 5 | Position 6 | Position 7 | C-terminal |
|---|---|---|---|---|---|---|---|
| B40 (B60, 61) | | | | | | | M, T, R |
| HLA-B42 | | L, P | | | | | Y, L |
| HLA-B44 | | E | | | | | F, Y, W |
| HLA-B46 | | M, I, L, V | | | | | Y, F |
| HLA-B48 | | Q, K | | | | | L |
| HLA-B51 | | A, P, G | | | | | F, Y, I, V |
| HLA-B52 | | Q | F, Y | | | | I, V |
| HLA-B53 | | P | | | | | W, F, L |
| HLA-B54 | | P | | | | | |
| HLA-B55 | | P | | | | | A, V |
| HLA-B56 | | P | | | | | A, V |
| HLA-B57 | | A, T, S | | | | | F, W, Y |
| HLA-B58 | | A, T, S | | | | | F, W, Y |
| HLA-B67 | | P | | | | | L |
| HLA-B73 | | R | | | | | P |
| HLA-Cw1 | | A, L | | | | | L |
| HLA-Cw2 | | A, L | | | | | F, Y |
| HLA-Cw3 | | A, L | | | | | L, M |
| HLA-Cw4 | | Y, P, F | | | | | L, M, F, Y |
| HLA-Cw6 | | Y | | | | | L, Y, F, Y |
| HLA-Cw8 | | Y | | | | | L, I, |
| HLA-Cw16. | | A, L | | | | | L, V |

19. The peptide according to claim 5 that is capable of eliciting INF-γ-producing cells in a PBL population of a cancer patient at a frequency of at least 10 per $10^4$ PBLs.

20. The peptide according to claim 5 which is capable of eliciting INF-γ-producing cells in a PBL population of a patient having a cancer disease where a protein belonging to the Bcl-2 protein family is expressed.

21. The peptide of claim 20 where the cancer disease is selected from the group consisting of a haematopoietic malignancy, melanoma, breast cancer, cervix cancer, ovary cancer, lung cancer, colon cancer, pancreas cancer and prostate cancer.

22. The vaccine composition according to claim 1 comprising a peptide which is an isolated immunogenically active peptide derived from a protein belonging to the Bcl-2 protein family.

23. The vaccine composition of claim 22 wherein said peptide has a $C_{50}$ value which is at the most 30 μl.

24. The vaccine composition according to claim 1 where the vaccine elicits the production in a vaccinated patient of effector T-cells having a cytotoxic effect against the cancer cells.

25. The vaccine composition according to claim 1 further comprising an immunogenic protein or peptide fragment selected from a protein or peptide fragment not belonging to or derived from the Bcl-2 protein family.

26. The vaccine composition of claim 25 where the protein or peptide fragment not belonging to or derived from the Bcl-2 protein family is a protein involved in regulation of cell apoptosis or a peptide fragment derived therefrom.

27. The vaccine composition of claim 25 where the immunogenic protein or peptide fragment selected from a protein or peptide fragment not belonging to or derived from the Bcl-2 protein family is survivin or a peptide fragment thereof.

28. The vaccine composition of claim 25 where the immunogenic protein or peptide fragment selected from a protein or peptide fragment not belonging to or derived from the Bcl-2 protein family is ML-IAP or a peptide fragment thereof.

29. The vaccine composition according to claim 1, wherein the composition comprises an adjuvant.

30. The vaccine composition according to claim 29, wherein the adjuvant is selected from the group consisting of bacterial DNA based adjuvants, oil/surfactant based adjuvants, viral dsRNA based adjuvants and imidazochinilines.

31. The vaccine composition according to claim 1, wherein the vaccine composition further comprises antigen presenting cells comprising the peptide of claim 1.

32. The vaccine composition according to claim 31, wherein the antigen presenting cell is a dendritic cell.

33. The vaccine composition according to claim 1, wherein the composition comprises a liposome.

34. The vaccine composition according to claim 1, furthermore comprising a T-cell stimulatory polypeptide.

35. The vaccine composition according to claim 34, wherein the T-cell stimulatory polypeptide is selected from the group consisting of B7.1, ICAM-1 and LFA-3.

36. A kit-of-parts comprising the vaccine composition according to claim 34, and a further anti-cancer agent.

37. The kit-of-parts according to claim 36, wherein the anti-cancer agent is an antibody.

38. The kit-of-parts according to claim 37, wherein the anti-cancer agent is a cytokine.

39. A composition for ex vivo or in situ diagnosis of the presence in a cancer patient of T cells in PBL or in tumor tissue that are reactive with a Bcl-2 protein family member, the composition comprising a peptide according to claim 5.

40. A diagnostic kit for ex vivo or in situ diagnosis of the presence in a cancer patient of T cells in PBL or in tumor tissue that are reactive with a Bcl-2 protein family member, the kit comprising a peptide according to claim 5.

41. A complex of a peptide according to claim 5 and a Class I HLA molecule or a fragment of such molecule.

42. The complex of claim 41 which is monomeric.

43. The complex of claim 41 which is multimeric.

44. The peptide of claim 5 which consists of SEQ ID NO:8.

45. The vaccine composition of claim 1, wherein the peptide is capable of raising a BC12-specific T-cell response.

46. The peptide of claim 14 which is a fragment of Bcl-2.

47. The peptide of claim 5 which comprises a sequence which differs from SEQ ID NO:8, if at all, by a single amino acid substitution.

48. The peptide of claim 5, which comprises a sequence which differs from SEQ ID NO:8 only at residues other than residues 2, 6 and 10 of SEQ ID NO:8.

49. The peptide of claim 5, which comprises a sequence which, if it differs from SEQ ID NO:8, is such that the residue corresponding to residue 2 of SEQ ID NO:8 is L or M, and the residue corresponding to residue 10 of SEQ ID NO:8 is L or V.

50. The peptide of claim 5, which, if it differs from SEQ ID NO:8, at least one such difference is that the residue corresponding to residue 6 of SEQ ID NO:8 is V.

51. The peptide of claim 47, which comprises a sequence which differs from SEQ ID NO:8 only at residues other than residues 2, 6 and 10 of SEQ ID NO:8.

52. The peptide of claim 47, which comprises a sequence which, if it differs from SEQ ID NO:8 is such that the residue corresponding to residue 2 of SEQ ID NO:8 is L or M, and the residue corresponding to residue 10 of SEQ ID NO:8 is L or V.

53. The peptide of claim 5, which, if it differs from SEQ ID NO:8, said difference is that the residue corresponding to residue 6 of SEQ ID NO:8 is V.

* * * * *